US012630605B2

(12) United States Patent
Hu

(10) Patent No.: US 12,630,605 B2
(45) Date of Patent: May 19, 2026

(54) TISSUE FACTOR-TARGETING CAR-NK AND CAR-T CELL THERAPY

(71) Applicant: Ohio State Innovation Foundation, Columbus, OH (US)

(72) Inventor: Zhiwei Hu, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 260 days.

(21) Appl. No.: 16/651,512

(22) PCT Filed: Sep. 17, 2018

(86) PCT No.: PCT/US2018/051344
§ 371 (c)(1),
(2) Date: Mar. 27, 2020

(87) PCT Pub. No.: WO2019/067249
PCT Pub. Date: Apr. 4, 2019

(65) Prior Publication Data
US 2020/0352996 A1      Nov. 12, 2020

Related U.S. Application Data

(60) Provisional application No. 62/564,006, filed on Sep. 27, 2017.

(51) Int. Cl.
| | |
|---|---|
| C07K 14/705 | (2006.01) |
| A61K 40/15 | (2025.01) |
| A61K 40/31 | (2025.01) |
| A61K 40/42 | (2025.01) |
| A61P 35/00 | (2006.01) |
| A61P 35/02 | (2006.01) |
| C07K 14/725 | (2006.01) |
| C07K 14/745 | (2006.01) |
| C07K 16/36 | (2006.01) |
| C12N 5/0783 | (2010.01) |
| A61K 38/00 | (2006.01) |
| A61K 39/00 | (2006.01) |

(52) U.S. Cl.
CPC ........ C07K 14/70521 (2013.01); A61K 40/15 (2025.01); A61K 40/31 (2025.01); A61K 40/4249 (2025.01); A61P 35/00 (2018.01); A61P 35/02 (2018.01); C07K 14/7051 (2013.01); C07K 14/70578 (2013.01); C07K 14/745 (2013.01); C07K 16/36 (2013.01); C12N 5/0646 (2013.01); A61K 38/00 (2013.01); *A61K 2039/505* (2013.01); *A61K 2239/17* (2023.05); *A61K 2239/31* (2023.05); *A61K 2239/38* (2023.05); *A61K 2239/49* (2023.05); *C07K 2317/622* (2013.01); *C07K 2317/732* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,399,346 A | 3/1995 | Anderson et al. | |
| 6,924,359 B1 | 8/2005 | Garen et al. | |
| 7,446,190 B2 | 11/2008 | Sadelain et al. | |
| 8,389,282 B2 | 3/2013 | Sadelain et al. | |
| 9,758,776 B2 | 9/2017 | Schellenberger et al. | |
| 10,273,300 B2 * | 4/2019 | Bedoya ............. | C07K 16/2803 |
| 2011/0046060 A1 | 2/2011 | Schellenberger et al. | |
| 2012/0148552 A1 | 6/2012 | Jensen | |
| 2012/0208759 A1 | 8/2012 | Fima et al. | |
| 2016/0158359 A1 * | 6/2016 | Gilbert ................... | A61P 37/04 |
| | | | 424/134.1 |
| 2016/0362672 A1 | 12/2016 | Schellenberger et al. | |

FOREIGN PATENT DOCUMENTS

| | | |
|---|---|---|
| CN | 102875685 A | 1/2013 |
| CN | 102875685 B | 1/2013 |
| JP | 2003-504315 A | 2/2003 |
| JP | 2013-534427 A | 9/2013 |
| WO | 0102439 A1 | 1/2001 |
| WO | 2004/006962 A2 | 1/2004 |
| WO | 2012006633 A1 | 1/2012 |
| WO | 2016/174461 A1 | 3/2016 |
| WO | 2016/210447 A1 | 12/2016 |
| WO | 2017/015582 A1 | 1/2017 |
| WO | 2018/170134 A1 | 9/2018 |

OTHER PUBLICATIONS

Zhang, Qing et al. Oncotarget vol. 8,6 (2017): 9488-9499. doi:10.18632/oncotarget.14367 (Year: 2017).*
Zhang, Qing et al. Oncotarget vol. 8,6 (2016): 9488-9499. doi:10.18632/oncotarget. 14367 (Year: 2016).*
Chen, Xilin et al. Oncotarget vol. 7,19 (2016): 27764-77. doi:10.18632/oncotarget.8526 (Year: 2017).*
Hombach, Hombach, and H. Abken. Gene therapy 17.10 (2010): 1206-1213 (Year: 2010).*
Zhang, Cheng, et al. Biomarker research 5.1 (2017): 1-6. (Year: 2017).*
Stryer, Biochemistry 4th, WH Freeman, New York. 1995 (Year: 1995).*

(Continued)

*Primary Examiner* — Michael Szperka
*Assistant Examiner* — Lia E Taylor
(74) *Attorney, Agent, or Firm* — Meunier Carlin & Curfman LLC

(57)      ABSTRACT

Disclosed are methods and compositions related to chimeric antigen receptors (CARs) that recognize Tissue Factor (TF). Specifically, disclosed are CARs that comprise fVII or a functional fragment thereof. Also disclosed are immune effector cells comprising the CARs disclosed herein.

2 Claims, 10 Drawing Sheets

Specification includes a Sequence Listing.

(56) References Cited

OTHER PUBLICATIONS

Portillo, Ana L et al. "Expanded human NK cells armed with CAR uncouple potent anti-tumor activity from off-tumor toxicity against solid tumors." iScience vol. 24,6 102619. May 24, 2021, doi:10.1016/j.isci.2021.102619 (Year: 2021).*

Li, Ye et al. "Human iPSC-Derived Natural Killer Cells Engineered with Chimeric Antigen Receptors Enhance Anti-tumor Activity." Cell stem cell vol. 23,2 (2018): 181-192.e5. doi:10.1016/j.stem.2018.06.002 (Year: 2018).*

Albinger, Nawid et al. "Primary CD33-targeting CAR-NK cells for the treatment of acute myeloid leukemia." Blood cancer journal vol. 12,4 61. Apr. 13, 2022, doi:10.1038/s41408-022-00660-2 (Year: 2022).*

Hombach, Andreas A., and Hinrich Abken. "Of chimeric antigen receptors and antibodies: OX40 and 41BB costimulation sharpen up T cell-based immunotherapy of cancer." Immunotherapy 5.7 (2013): 677-681 (Year: 2013).*

Boissel, Laurent, et al. "Transfection with mRNA for CD19 specific chimeric antigen receptor restores NK cell mediated killing of CLL cells." Leukemia research 33.9 (2009): 1255-1259. (Year: 2009).*

Chu, Jianhong, et al. "CS1-specific chimeric antigen receptor (CAR)-engineered natural killer cells enhance in vitro and in vivo antitumor activity against human multiple myeloma." Leukemia 28.4 (2014): 917-927. (Year: 2014).*

Extended European Search Report issued by the European Patent Office in European Application No. 18860547.1 on Jun. 23, 2021. 9 pages.

International Search Report and Written Opinion issued by the International Searching Authority (ISA/US) in PCT Application No. PCT/US2018/051344 on Nov. 26, 2018. 13 pages.

Zhang, Qing, et al. "Chimeric antigen receptor-modified T Cells inhibit the growth and metastases of established tissue factor-positive tumors in NOG mice." Oncotarget 8.6 (2017): 9488.

Hu, Zhiwei, and Jing Li. "Natural killer cells are crucial for the efficacy of Icon (factor VII/human IgG1 Fc) Immunotherapy in human tongue cancer." BMC immunology 11.1 (2010): 49.

Abdulkadir, S.A., et al., Tissue factor expression and angiogenesis in human prostate carcinoma. Hum Pathol, 2000. 31(4): p. 443-7.

Adorno-Cruz, V., et al., Cancer stem cells: targeting the roots of cancer, seeds of metastasis, and sources of therapy resistance. Cancer Res, 2015. 75(6): p. 924-9.

Afuwape, A.O., S. Kiriakidis, and E.M. Paleolog, The role of the angiogenic molecule VEGF in the pathogenesis of rheumatoid arthritis. Histol Histopathol, 2002. 17(3): p. 961-72.

Akashi, T., et al., Tissue factor expression and prognosis in patients with metastatic prostate cancer. Urology, 2003. 62(6): p. 1078-82.

Altomare, D.F., et al., Tissue factor and vascular endothelial growth factor expression in colorectal cancer: relation with cancer recurrence. Colorectal Dis, 2007.9(2): p. 133-8.

Anders, et al., Biology, metastatic patterns, and treatment of patients with triple-negative breast cancer. Clinical breast cancer 9 Suppl 2, S73-81 (2009).

Anderson, W. French. Prospects for human gene therapy. Science 226.4673 (1984): 401-409.

Andoh, K., et al., Tissue factor activity in leukemia cells. Special reference to disseminated intravascular coagulation. Cancer, 1987. 59(4): p. 748-54.

Baggio, L., et al., Natural killer cell adoptive immunotherapy: Coming of age. Clin Immunol, 2017. 177: p. 3-11.

Bauer, K.A., et al., Tissue factor gene expression in acute myeloblastic leukemia. Thromb Res, 1989. 56(3): p. 425-30.

Bayraktar, et al., Molecularly targeted therapies for metastatic triple-negative breast cancer. Breast cancer research and treatment 138, 21-35 (2013).

Benaroch, P., et al., HIV-1 assembly in macrophages. Retrovirology, 2010. 7: p. 29.

Berrada, et al., Treatment of triple-negative metastatic breast cancer: toward individualized targeted treatments or chemosensitiza-tion? Annals of oncology: official journal of the European Society for Medical Oncology / ESMO 21 Suppl 7, vii30-35 (2010).

Bledsoe, J.G. and S.M. Slack, Tissue factor expression by rat osteosarcoma cells adherent to tissue culture polystyrene and selected orthopedic biomaterials. J Biomater Sci Polym Ed, 1998. 9(12): p. 1305-12.

Blömer, Ulrike, et al. Highly efficient and sustained gene transfer in adult neurons with a lentivirus vector. Journal of virology 71.9 (1997): 6641-6649.

Bora, P.S., et al., Immunotherapy for choroidal neovascularization in a laser-induced mouse model simulating exudative (wet) macular degeneration. Proc Natl Acad Sci U S A, 2003. 100(5): p. 2679-84.

Bregni, Marco, et al. Human peripheral blood hematopoietic progenitors are optimal targets of retroviral-mediated gene transfer. (1992): 1418-1422.

Breij, E.C., et al., An antibody-drug conjugate that targets tissue factor exhibits potent therapeutic activity against a broad range of solid tumors. Cancer Res, 2014. 74(4): p. 1214-26.

Brenchley, J.M., et al., Microbial translocation is a cause of systemic immune activation in chronic HIV infection. Nat Med, 2006. 12(12): p. 1365-71.

Brigham, Kenneth L., et al. Rapid communication: In vivo transfection of murine lungs with a functioning prokaryotic gene using a liposome vehicle. The American journal of the medical sciences 298.4 (1989): 278-281.

Bromberg, et al., Tissue factor promotes melanoma metastasis by a pathway independent of blood coagulation. Proceedings of the National Academy of Sciences of the United States of America 92, 8205-8209 (1995).

Busso, N., et al., Role of the tissue factor pathway in synovial inflammation. Arthritis Rheum, 2003. 48(3): p. 651-9.

Caine, et al., The hypercoagulable state of malignancy: pathogenesis and current debate. Neoplasia 4, 465-473 (2002).

Callander, N.S., N. Varki, and L.V. Rao, Immunohistochemical identification of tissue factor in solid tumors. Cancer, 1992. 70(5): p. 1194-201.

Camera, M., et al., The Role of Tissue Factor in Atherothrombosis and Coronary Artery Disease: Insights into Platelet Tissue Factor. Semin Thromb Hemost, 2015. 41(7): p. 737-46.

Camerer, E., A.B. Kolsto, and H. Prydz, Cell biology of tissue factor, the principal initiator of blood coagulation. Thromb Res, 1996. 81(1): p. 1-41.

Cayouette, Michel, and Claude Gravel. Adenovirus-mediated gene transfer of ciliary neurotrophic factor can prevent photoreceptor degeneration in the retinal degeneration (rd) mouse. Human gene therapy 8.4 (1997): 423-430.

Chen et al., A combinational therapy of EGFR-CAR NK cells and oncolytic herpes simplex virus 1 for breast cancer brain metastases. Oncotarget 7, 27764-27777 (2016).

Chen, L., et al., Tissue factor expression in rheumatoid synovium: a potential role in pannus invasion of rheumatoid arthritis. Acta Histochem, 2013, 692.

Cheng, J., et al., Effective treatment of human lung cancer by targeting tissue factor with a factor VII-targeted photodynamic therapy. Curr Cancer Drug Targets, 2011. 11(9): p. 1069-81.

Christmas, N.J., A Phase 2 Study (EMERGE) Evaluating Repeated Intravitreal Administration of ICON-1 in Patients With Choroidal Neovascularization (CNV) Secondary to Age-related Macular Degeneration (AMD). Investigative Ophthalmology & Visual Science, 2016. 57(12), 4434.

Clarke et al., Cancer stem cells—perspectives on current status and future directions: AACR Workshop on cancer stem cells. Cancer research 66, 9339-9344 (2006).

Cocco, E., et al., hI-con1, a factor VII-IgGFc chimeric protein targeting tissue factor for immunotherapy of uterine serous papillary carcinoma. Br J Cancer, 2010. 103(6): p. 812-9.

Colville-Nash, P.R. and D.L. Scott, Angiogenesis and rheumatoid arthritis: pathogenic and therapeutic implications. Ann Rheum Dis, 1992. 51(7): p. 919-25.

Contrino, J., et al., In situ characterization of antigenic and functional tissue factor expression in human tumors utilizing monoclonal antibodies and recombinant factor VIIa as probes. Am J Pathol, 1994. 145(6): p. 1315-22.

(56) References Cited

OTHER PUBLICATIONS

Contrino, J., et al., In situ detection of tissue factor in vascular endothelial cells: correlation with the malignant phenotype of human breast disease. Nat Med, 1996. 2(2): p. 209-15.

Cornetta et al., Nucleic Acid Research and Molecular Biology 36:311-322, 1987.

Danos, Olivier, and Richard C. Mulligan. Safe and efficient generation of recombinant retroviruses with amphotropic and ecotropic host ranges. Proceedings of the National Academy of Sciences 85.17 (1988): 6460-6464.

De Goeij, B.E., et al., High turnover of tissue factor enables efficient intracellular delivery of antibody-drug conjugates. Mol Cancer Ther, 2015. 14(5): p. 1130-40.

Dorner, T. and G.R. Burmester, The role of B cells in rheumatoid arthritis: mechanisms and therapeutic targets. Curr Opin Rheumatol, 2003. 15(3): p. 246-52.

Dorner, T. and P.E. Lipsky, B-cell targeting: a novel approach to immune intervention today and tomorrow. Expert Opin Biol Ther, 2007. 7(9): p. 1287-99.

Dorner, T., et al., Current status on B-cell depletion therapy in autoimmune diseases other than rheumatoid arthritis. Autoimmun Rev, 2009. 9(2): p. 82-9.

Dorner, T., N. Kinnman, and P.P. Tak, Targeting B cells in immune-mediated inflammatory disease: a comprehensive review of mechanisms of action and identification of biomarkers. Pharmacol Ther, 2010. 125(3): p. 464-75.

Duanmu, J., et al., Effective treatment of chemoresistant breast cancer in vitro and in vivo by a factor VII-targeted photodynamic therapy. Br J Cancer, 2011. 104(9): p. 1401-9.

Dupont, Jakob, et al. "Artificial Antigen-Presenting Cells Transduced with Telomerase Efficiently Expand Epitope-Specific, Human Leukocyte Antigen-Restricted Cytotoxic T Cells." Cancer research 65.12 (2005): 5417-5427.

Eglitis, Martin A., and W. French Anderson. "Retroviral vectors for introduction of genes in to mammalian cells." Biotechniques 6.7 (1988): 608-614.

El Guerrab et al., Differential impact of EGFR-targeted therapies on hypoxia responses: implications for treatment sensitivity in triple-negative metastatic breast cancer. PloS one 6, e25080 (2011).

Fauriat, C., F. Mallet, and D. Olive. Impaired activating receptor expression pattern in natural killer cells from patients with multiple myeloma. Leukemia 20.4 (2006): 732-733.

Felgner, Philip L., et al. "Lipofection: a highly efficient, lipid-mediated DNA-transfection procedure." Proceedings of the National Academy of Sciences 84.21 (1987): 7413-7417.

Ferrandina, G., et al., Targeting CD133 antigen in cancer. Expert Opin Ther Targets, 2009. 13(7): p. 823-37.

Ferrara, N., VEGF and the quest for tumour angiogenesis factors. Nat Rev Cancer, 2002. 2(10): p. 795-803.

Folkman, J., Angiogenesis in cancer, vascular, rheumatoid and other disease. Nat Med, 1995. 1(1): p. 27-31.

Folkman, J., Tumor angiogenesis and tissue factor. Nat Med, 1996. 2(2): p. 167-8.

Folkman, J., Tumor angiogenesis: therapeutic implications. N Engl J Med, 1971. 285(21): p. 1182-6.

Freeburn, J.C., W.S. Gilmore, and J.J. Strain, The effect of cytokines on tissue factor expression in HL-60 and U937 cell lines. Biochem Soc Trans, 1995. 23(2): p. 286S.

Friedl, J., et al., Induction of permeability across endothelial cell monolayers by tumor necrosis factor (TNF) occurs via a tissue factor-dependent mechanism: relationship between the procoagulant and permeability effects of TNF. Blood, 2002. 100(4): p. 1334-9.

Friedmann, Theodore. "Progress toward human gene therapy." Science 244.4910 (1989): 1275-1281.

Fujimoto, J., et al., Angiogenesis in endometriosis and angiogenic factors. Gynecol Obstet Invest, 1999. 48 Suppl 1: p. 14-20.

Funderburg, N.T., et al., Increased tissue factor expression on circulating monocytes in chronic HIV infection: relationship to in vivo coagulation and immune activation. Blood, 2010. 115(2): p. 161-7.

Gay, F., et al., Immuno-oncologic Approaches: CAR-T Cells and Checkpoint Inhibitors. Clin Lymphoma Myeloma Leuk, 2017. 17(8): p. 471-478.

Geisbert, T.W., et al., Mechanisms underlying coagulation abnormalities in ebola hemorrhagic fever: overexpression of tissue factor in primate monocytes/macrophages is a key event. J Infect Dis, 2003. 188(11): p. 1618-29.

Geisbert, T.W., et al., Treatment of Ebola virus infection with a recombinant inhibitor of factor VIIa/tissue factor: a study in rhesus monkeys. Lancet, 2003. 362(9400): p. 1953-8.

Godfrey, James, and Don M. Benson Jr. "The role of natural killer cells in immunity against multiple myeloma." Leukemia & lymphoma 53.9 (2012): 1666-1676.

Grabowski, E.F., D.B. Zuckerman, and Y. Nemerson, The functional expression of tissue factor by fibroblasts and endothelial cells under flow conditions. Blood, 1993. 81(12): p. 3265-70.

Grossniklaus, H.E., et al., Macrophage and retinal pigment epithelium expression of angiogenic cytokines in choroidal neovascularization. Mol Vis, 2002. 8: p. 119-26.

Guan, M., et al., Tissue factor expression and angiogenesis in human glioma. Clin Biochem, 2002. 35(4): p. 321-5.

Hair, G.A., et al., Tissue factor expression in human leukemic cells. Leuk Res, 1996. 20(1): p. 1-11.

Hamada, K., et al., Expression of tissue factor correlates with grade of malignancy in human glioma. Cancer, 1996. 77(9): p. 1877-83.

Hanahan, D. and R.A. Weinberg, Hallmarks of cancer: the next generation. Cell, 2011. 144(5): p. 646-74.

Hanahan, D. and R.A. Weinberg, The hallmarks of cancer. Cell, 2000. 100(1): p. 57-70.

Herbert, J.M., et al., IL-4 inhibits LPS-, IL-1 beta- and TNF alpha-induced expression of tissue factor in endothelial cells and monocytes. FEBS Lett, 1992. 310(1): p. 31-3.

Herbert, J.M., et al., Malformin-A1 inhibits the binding of interleukin-1 beta (IL1 beta) and suppresses the expression of tissue factor in human endothelial cells and monocytes. Biochem Pharmacol, 1994. 48(6): p. 1211-7.

Hu Z, Rao B, Chen S and Duanmu J. Selective and effective killing of angiogenic vascular endothelial cells and cancer cells by targeting tissue factor using a factor VII-targeted photodynamic therapy for breast cancer. Breast cancer research and treatment. 2011; 126(3):589-600.

Hu, et al., Intratumoral injection of adenoviral vectors encoding tumor-targeted immunoconjugates for cancer immunotherapy. Proceedings of the National Academy of Sciences of the United States of America 97, 9221-9225 (2000).

Hu, et al., Targeting Tissue Factor for Immunotherapy of Triple-Negative Breast Cancer Using a Second-Generation ICON. Cancer Immunol Res 6, 671-684 (2018).

Hu, et al., Therapeutic Antibody-Like Immunoconjugates against Tissue Factor with the Potential to Treat Angiogenesis-Dependent as Well as Macrophage-Associated Human Diseases. Antibodies 7, (2018).

Hu, Y., Tian, Z.G., and Zhang, C. (2018). Chimeric antigen receptor (CAR)-transduced natural killer cells in tumor immunotherapy. Acta Pharmacol Sin 39, 167-176.

Hu, Z. and A. Garen, Targeting tissue factor on tumor vascular endothelial cells and tumor cells for immunotherapy in mouse models of prostatic cancer. Proc Natl Acad Sci U S A, 2001. 98(21): p. 12180-5.

Hu, Z. and J. Li, Natural killer cells are crucial for the efficacy of Icon (factor VII/human IgG1 Fc) immunotherapy in human tongue cancer. BMC Immunol, 2010. 11: p. 49.

Hu, Z., et al., Assessing the carcinogenic potential of low-dose exposures to chemical mixtures in the environment: focus on the cancer hallmark of tumor angiogenesis. Carcinogenesis, 2015. 36 Suppl 1: p. S184-202.

Hu, Z., et al., Targeting tissue factor as a novel therapeutic oncotarget for eradication of cancer stem cells isolated from tumor cell lines, tumor xenografts and patients of breast, lung and ovarian cancer. Oncotarget, 2017. 8(1): p. 1481-1494.

(56)  References Cited

OTHER PUBLICATIONS

Hu, Z., et al., Targeting tissue factor on tumour cells and angiogenic vascular endothelial cells by factor VII-targeted verteporfin photodynamic therapy for breast cancer in vitro and in vivo in mice. BMC Cancer, 2010. 10: p. 235.

Hu, Z., et al., Tissue factor is an angiogenic-specific receptor for factor VII-targeted immunotherapy and photodynamic therapy. Angiogenesis, 2017. 20(1): p. 85-96.

Hu, Z., Factor VII-Targeted Photodynamic Therapy for Breast Cancer and Its Therapeutic Potential for Other Solid Cancers and Leukemia, Breast Cancer—Current and Alternative Therapeutic Modalities, Esra Gunduz and Mehmet Gunduz (Ed.), ISBN: 978-953-307-776-5, InTech, Available from: http://www.intechopen.com/articles/show/title/factor-vii-targeted-photodynamic-therapy-for-breast-cancer-and-its-therapeutic-potential-for-other-s. Breast Cancer—Current and Alternative Therapeutic Modalities, ed. E. Gunduz, Gunduz, M. 2011: InTech. 175-196.

Hu, Z., Y. Sun, and A. Garen, Targeting tumor vasculature endothelial cells and tumor cells for immunotherapy of human melanoma in a mouse xenograft model. Proc Natl Acad Sci U S A, 1999. 96(14): p. 8161-6.

Hudis, et al., Triple-negative breast cancer: an unmet medical need. The oncologist 16 Suppl 1, 1-11 (2011).

Hufnagel et al., Icon immunoconjugate treatment results in regression of red lesions in a non-human primate (Papio anubis) model of endometriosis. Reprod Biol 18, 109-114 (2018).

Hughes, P. F., et al. Retroviral gene transfer to primitive normal and leukemic hematopoietic cells using clinically applicable procedures. The Journal of clinical investigation 89.6 (1992): 1817-1824.

Jemal et al., Global cancer statistics. CA: a cancer journal for clinicians 61, 69-90 (2011).

Johnson, Larry G. "Gene therapy for cystic fibrosis." Chest 107.2 (1995): 77S-83S.

Juarez, M., A. Filer, and C.D. Buckley, Fibroblasts as therapeutic targets in rheumatoid arthritis and cancer. Swiss Med Wkly, 2012. 142: p. w13529.

Kageshita, T., et al., Tissue factor expression and serum level in patients with melanoma does not correlate with disease progression. Pigment Cell Res, 2001. 14(3): p. 195-200.

Kaido, T., et al., Tissue factor is a useful prognostic factor of recurrence in hepatocellular carcinoma in 5-year survivors. Hepatogastroenterology, 2005. 52(65): p. 1383-7.

Kakkar, A.K., et al., Tissue factor expression correlates with histological grade in human pancreatic cancer. Br J Surg, 1995. 82(8): p. 1101-4.

Kassam et al., Survival outcomes for patients with metastatic triple-negative breast cancer: implications for clinical practice and trial design. Clinical breast cancer 9, 29-33 (2009).

Kasthuri, M. B. Taubman, N. Mackman, Role of tissue factor in cancer. J Clin Oncol 27, 4834-4838 (2009).

Kaushal, V., et al., Expression of tissue factor in prostate cancer correlates with malignant phenotype. Appl Immunohistochem Mol Morphol, 2008. 16(1): p. 1-6.

Khorana, A.A., et al., Tissue factor expression, angiogenesis, and thrombosis in pancreatic cancer. Clin Cancer Res, 2007. 13(10): p. 2870-5.

Kido, M., et al. "Use of a retroviral vector with an internal opsin promoter to direct gene expression to retinal photoreceptor cells." Current eye research 15.8 (1996): 833-844.

Kim, et al. Mapping the site on human IgG for binding of the MHC class I-related receptor, FcRn. European journal of immunology 29, 2819-2825, doi:10.1002/(SICI)1521-4141(199909)29:09<2819::Aid-IMMU2819>3.0.CO;2-6 (1999).

Klagsbrun, M., et al., Purification of endothelial cell growth factors by heparin affinity chromatography. Methods Enzymol, 1987. 147: p. 95-105.

Koch U, Krause M and Baumann M. Cancer stem cells at the crossroads of current cancer therapy failures—radiation oncology perspective. Seminars in cancer biology. 2010; 20(2):116-124.

Konigsberg, W.H. and Y. Nemerson, Molecular cloning of the cDNA for human tissue factor. Cell, 1988. 52(5): p. 639-40.

Koomagi, R. and M. Volm, Tissue-factor expression in human non-small-cell lung carcinoma measured by immunohistochemistry: correlation between tissue factor and angiogenesis. Int J Cancer, 1998. 79(1): p. 19-22.

Kremer, V., et al., Genetic engineering of human NK cells to express CXCR2 improves migration to renal cell carcinoma. J Immunother Cancer, 2017. 5(1): p. 73.

Krikun, G., Endometriosis, angiogenesis and tissue factor. Scientifica (Cairo), 2012. 2012: p. 306830.

Krikun, G., et al., Endometriosis and tissue factor. Ann N Y Acad Sci, 2008. 1127: p. 101-5.

Krikun, G., et al., The immunoconjugate "icon" targets aberrantly expressed endothelial tissue factor causing regression of endometriosis. Am J Pathol, 2010. 176(2): p. 1050-6.

Kubota, T., et al., Tissue factor released from leukemic cells. Thromb Haemost, 1991. 65(1): p. 59-63.

La Salle, G. Le Gal, et al. An adenovirus vector for gene transfer into neurons and glia in the brain. Science 259.5097 (1993): 988-990.

Lewis, J.C., et al., Tissue factor expression during coculture of endothelial cells and monocytes. Exp Mol Pathol, 1995. 62(3): p. 207-18.

Liedtke, et al., Current Issues of Targeted Therapy in Metastatic Triple-Negative Breast Cancer. Breast care 6, 234-239 (2011).

Liu, E., Tong, Y., Dotti, G., Shaim, H., Savoldo, B., Mukherjee, M., Orange, J., Wan, X., Lu, X., Reynolds, A., et al. (2018). Cord blood NK cells engineered to express IL-15 and a CD19-targeted CAR show long-term persistence and potent antitumor activity. Leukemia 32, 520-531.

Lockwood, C.J., et al., The role of tissue factor in regulating endometrial haemostasis: implications for progestin-only contraception. Hum Reprod, 2000. 15 Suppl 3: p. 144-51.

Lopez-Pedrera, C., et al., Tissue factor as an effector of angiogenesis and tumor progression in hematological malignancies. Leukemia, 2006. 20(8): p. 1331-40.

Luther, T., et al., Flow cytometric analysis of tissue factor (TF) expression on stimulated monocytes—comparison to procoagulant activity of mononuclear blood cells. Blut, 1990. 61(6): p. 375-8.

Lykke, e al., The role of tissue factor in colorectal cancer. Eur J Surg Oncol 29, 417-422 (2003).

Marrelli, A., et al., Angiogenesis in rheumatoid arthritis: A disease specific process or a common response to chronic inflammation? Autoimmun Rev, 2011.

Maruotti, N., et al., Angiogenesis in rheumatoid arthritis. Histol Histopathol, 2006. 21(5): p. 557-66.

Mayr, M., et al., Proteomics, metabolomics, and immunomics on microparticles derived from human atherosclerotic plaques. Circ Cardiovasc Genet, 2009. 2(4): p. 379-88.

Mechiche, H. and P. Nguyen, IL-4 modulates tissue factor expression by human B lymphocytes in response to phorbol myristate acetate. Thromb Haemost, 2007. 97(1): p. 158-9.

Mechiche, H., P. Cornillet-Lefebvre, and P. Nguyen, A subpopulation of human B lymphocytes can express a functional Tissue Factor in response to phorbol myristate acetate. Thromb Haemost, 2005. 94(1): p. 146-54.

Meerarani, P., et al., Atherothrombosis: role of tissue factor; link between diabetes, obesity and inflammation. Indian J Exp Biol, 2007. 45(1): p. 103-10.

Mehta, R.S., and Rezvani, K. (2018). Chimeric Antigen Receptor Expressing Natural Killer Cells for the Immunotherapy of Cancer. Front Immunol 9, 283.

Miller, A. Dusty, and Guy J. Rosman. "Improved retroviral vectors for gene transfer and expression." Biotechniques 7.9 (1989): 980.

Miller, A. D., M. F. Law, and I. M. Verma. "Generation of helper-free amphotropic retroviruses that transduce a dominant-acting, methotrexate-resistant dihydrofolate reductase gene." Molecular and cellular biology 5.3 (1985): 431-437.

Miller, A. Dusty, and C. A. R. O. L. Buttimore. "Redesign of retrovirus packaging cell lines to avoid recombination leading to helper virus production." Molecular and Cellular Biology 6.8 (1986): 2895-2902.

(56)     References Cited

OTHER PUBLICATIONS

Miller, A. Dusty. "Retrovirus packaging cells." Human gene therapy 1.1 (1990): 5-14.

Milsom et al., Tissue factor and cancer stem cells: is there a linkage? Arterioscler Thromb Vasc Biol 29, 2005-2014 (2009).

Miyoshi, Hiroyuki, et al. "Stable and efficient gene transfer into the retina using an HIV-based lentiviral vector." Proceedings of the National Academy of Sciences 94.19 (1997): 10319-10323.

Moncharmont C, Levy A, Gilormini M, Bertrand G, Chargari C, Alphonse G, Ardail D, Rodriguez-Lafrasse C and Magne N. Targeting a cornerstone of radiation resistance: cancer stem cell. Cancer letters. 2012; 322(2):139-147.

Montero, et al., Bevacizumab in the treatment of metastatic breast cancer: friend or foe? Current oncology reports 14, 1-11 (2012).

Morello et al. Mesothelin-Targeted CARs: Driving T Cells to Solid Tumors. Cancer Discov, 2016. 6(2): p. 133-46.

Morgan, Richard A., et al. "Case report of a serious adverse event following the administration of T cells transduced with a chimeric antigen receptor recognizing ERBB2." Molecular Therapy 18.4 (2010): 843-851.

Morgan, Richard A., et al. "Cancer regression in patients after transfer of genetically engineered lymphocytes." Science 314.5796 (2006): 126-129.

Morrissey, J.H., H. Fakhrai, and T.S. Edgington, Molecular cloning of the cDNA for tissue factor, the cellular receptor for the initiation of the coagulation protease cascade. Cell, 1987. 50(1): p. 129-35.

Mousa, S.A., Role of current and emerging antithrombotics in thrombosis and cancer. Timely Top Med Cardiovasc Dis, 2006. 10: p. E19.

Nakasaki, T., et al., Decreased tissue factor and tissue-plasminogen activator antigen in relapsed acute promyelocytic leukemia. Am J Hematol, 2000. 64(3): p. 145-50.

Nakasaki, T., et al., Elevated tissue factor levels in leukemic cell homogenate. Clin Appl Thromb Hemost, 2000. 6(1): p. 14-7.

Nakasaki, T., et al., Expression of tissue factor and vascular endothelial growth factor is associated with angiogenesis in colorectal cancer. Am J Hematol, 2002. 69(4): p. 247-54.

Naldini, Luigi, et al. "In vivo gene delivery and stable transduction of nondividing cells by a lentiviral vector." Science 272.5259 (1996): 263-267.

Narni-Mancinelli, Emilie, Eric Vivier, and Yann M. Kerdiles. "The 'T-cell-ness' of NK cells: unexpected similarities between NK cells and T cells." International immunology 23.7 (2011): 427-431.

Nemerson, Y., Tissue factor and hemostasis. Blood, 1988. 71(1): p. 1-8.

Nemerson, Y., Tissue factor and the initiation of blood coagulation. Adv Exp Med Biol, 1987. 214: p. 83-94.

Nitori, N., et al., Prognostic significance of tissue factor in pancreatic ductal adenocarcinoma. Clin Cancer Res, 2005. 11(7): p. 2531-9.

Nowakowska, P., Romanski, A., Miller, N., Odendahl, M., Bonig, H., Zhang, C., Seifried, E., Wels, W.S., and Tonn, T. (2018). Clinical grade manufacturing of genetically modified, CAR-expressing NK-92 cells for the treatment of ErbB2-positive malignancies. Cancer Immunol Immunother 67, 25-38.

Osterud, B. and E. Bjorklid, The production and availability of tissue thromboplastin in cellular populations of whole blood exposed to various concentrations of endotoxin. An assay for detection of endotoxin. Scand J Haematol, 1982. 29(2): p. 175-84.

Owens, A.P., 3rd and N. Mackman, Role of tissue factor in atherothrombosis. Curr Atheroscler Rep, 2012. 14(5): p. 394-401.

Paleolog, E.M. and R.A. Fava, Angiogenesis in rheumatoid arthritis: implications for future therapeutic strategies. Springer Semin Immunopathol, 1998. 20(1-2): p. 73-94.

Paleolog, E.M., Angiogenesis in rheumatoid arthritis. Arthritis Res, 2002. 4 Suppl 3: p. S81-90.

Panelli, Monica C., et al. "A tumor-infiltrating lymphocyte from a melanoma metastasis with decreased expression of melanoma differentiation antigens recognizes MAGE-12." The Journal of Immunology 164.8 (2000): 4382-4392.

Panelli, Monica C., et al. "Expansion of tumor-T cell pairs from fine needle aspirates of melanoma metastases." The Journal of Immunology 164.1 (2000): 495-504.

Papanicolaou, Genovefa A., et al. "Rapid expansion of cytomegalovirus-specific cytotoxic T lymphocytes by artificial antigen-presenting cells expressing a single HLA allele." Blood 102.7 (2003): 2498-2505.

Paszkiewicz, et al., Targeted antibody-mediated depletion of murine CD19 CAR T cells permanently reverses B cell aplasia. J Clin Invest 126, 4262-4272 (2016).

Pecen, P.E. and P.K. Kaiser, Current phase 1/2 research for neovascular age-related macular degeneration. Curr Opin Ophthalmol, 2015. 26(3): p. 188-93.

Peitzsch, A et al., Cancer stem cells: The root of tumor recurrence and metastases. Semin Cancer Biol 44, 10-24 (2017).

Pendurthi, U.R., D. Alok, and L.V. Rao, Binding of factor VIIa to tissue factor induces alterations in gene expression in human fibroblast cells: up-regulation of poly(A) polymerase. Proc Natl Acad Sci U S A, 1997. 94(23): p. 12598-603.

Penka, [Activation of blood coagulation in oncology patients]. Vnitrni lekarstvi 43, 337-339 (1997). Abstract.

Phillips, et al., The response of CD24(-/low)/CD44+ breast cancer-initiating cells to radiation. Journal of the National Cancer Institute 98, 1777-1785 (2006).

Poon, R.T., et al., Tissue factor expression correlates with tumor angiogenesis and invasiveness in human hepatocellular carcinoma. Clin Cancer Res, 2003. 9(14): p. 5339-45.

Porter, David L., et al. "Chimeric antigen receptor-modified T cells in chronic lymphoid leukemia." N engl j Med 365 (2011): 725-733.

Presta, L., et al., Generation of a humanized, high affinity anti-tissue factor antibody for use as a novel antithrombotic therapeutic. Thromb Haemost, 2001. 85(3): p. 379-89.

Rak, J., et al., Tissue factor in cancer and angiogenesis: the molecular link between genetic tumor progression, tumor neovascularization, and cancer coagulopathy. Semin Thromb Hemost, 2006. 32(1): p. 54-70.

Rakha, et al., Metastatic triple-negative breast cancer. Clinical oncology 23, 587-600 (2011).

Rao, et al., Tissue factor on cells. Blood Coagul Fibrinolysis 9 Suppl 1, S27-35 (1998).

Rickles, et al., The role of the hemostatic system in tumor growth, metastasis, and angiogenesis: tissue factor is a bifunctional molecule capable of inducing both fibrin deposition and angiogenesis in cancer. Int J Hematol 73, 145-150 (2001).

Rickles, F.R., et al., Tissue factor expression in human leukocytes and tumor cells. Thromb Haemost, 1995. 74(1): p. 391-5.

Rosenberg et al., N. Engl. J. Med 323:370, 1990.

Rosenberg, Z.F. and A.S. Fauci, Immunopathogenesis of HIV infection. FASEB J, 1991. 5(10): p. 2382-90.

Ruf, et al., Tissue factor and cell signalling in cancer progression and thrombosis. J Thromb Haemost 9 Suppl 1, 306-315 (2011).

Sadelain, Michel, Isabelle Rivière, and Renier Brentjens. Targeting tumours with genetically enhanced T lymphocytes. Nature Reviews Cancer 3.1 (2003): 35-45.

Saha, D., et al., Tissue factor and atherothrombosis. Curr Pharm Des, 2015. 21(9): p. 1152-7.

Sawada, M., et al., Expression of tissue factor in non-small-cell lung cancers and its relationship to metastasis. Br J Cancer, 1999. 79(3-4): p. 472-7.

Schatz, F., et al., Progestin-regulated expression of tissue factor in decidual cells: implications in endometrial hemostasis, menstruation and angiogenesis. Steroids, 2003. 68(10-13): p. 849-60.

Schecter, A.D., et al., Tissue factor expression in human arterial smooth muscle cells. TF is present in three cellular pools after growth factor stimulation. J Clin Invest, 1997. 100(9): p. 2276-85.

Semeraro, et al., Tissue factor in health and disease. Thrombosis and haemostasis 78, 759-764 (1997).

Sharp, Gene Therapy. The Lancet 337: 1277-1278, 1991.

Sheridan et al., CD44+/CD24- breast cancer cells exhibit enhanced invasive properties: an early step necessary for metastasis. Breast Cancer Res 8, R59 (2006).

Shigemori, C., et al., Tissue factor expression and metastatic potential of colorectal cancer. Thromb Haemost, 1998. 80(6): p. 894-8.

(56) References Cited

OTHER PUBLICATIONS

Shoji, M., et al., Activation of coagulation and angiogenesis in cancer: immunohistochemical localization in situ of clotting proteins and vascular endothelial growth factor in human cancer. Am J Pathol, 1998. 152(2): p. 399-411.

Spicer, E.K., et al., Isolation of cDNA clones coding for human tissue factor: primary structure of the protein and cDNA. Proc Natl Acad Sci U S A, 1987. 84(15): p. 5148-52.

Spitzer, M.H., et al., Systemic Immunity Is Required for Effective Cancer Immunotherapy. Cell, 2017. 168(3): p. 487-502 e15.

Sridhar, P. and F. Petrocca, Regional Delivery of Chimeric Antigen Receptor (CAR) T-Cells for Cancer Therapy. Cancers (Basel), 2017. 9(7)).

Stapleton, et al. Competition for FcRn-mediated transport gives rise to short half-life of human IgG3 and offers therapeutic potential. Nature communications 2, 599, doi:10.1038/ncomms1608 (2011).

Straubinger, Robert M., and Demetrios Papahadjopoulos. [32] Liposomes as carriers for intracellular delivery of nucleic acids. Methods in enzymology. vol. 101. Academic Press, 1983. 512-527.

Stupack, D.G., C.M. Storgard, and D.A. Cheresh, A role for angiogenesis in rheumatoid arthritis. Braz J Med Biol Res, 1999. 32(5): p. 573-81.

Sturm, U., et al., Immunohistological detection of tissue factor in normal and abnormal human mammary glands using monoclonal antibodies. Virchows Arch A Pathol Anat Histopathol, 1992. 421(2): p. 79-86.

Szekanecz, Z. and A.E. Koch, Angiogenesis and its targeting in rheumatoid arthritis. Vascul Pharmacol, 2009. 51(1): p. 1-7.

Szekanecz, Z. and A.E. Koch, Endothelial cells in inflammation and angiogenesis. Curr Drug Targets Inflamm Allergy, 2005. 4(3): p. 319-23.

Szekanecz, Z., et al., Angiogenesis in rheumatoid arthritis. Autoimmunity, 2009. 42(7): p. 563-73.

Szekanecz, Z., G. Szegedi, and A.E. Koch, Angiogenesis in rheumatoid arthritis: pathogenic and clinical significance. J Investig Med, 1998. 46(2): p. 27-41.

Szekanecz, Z., L. Gaspar, and A.E. Koch, Angiogenesis in rheumatoid arthritis. Front Biosci, 2005. 10: p. 1739-53.

Takano, S., et al., Tissue factor, osteopontin, alphavbeta3 integrin expression in microvasculature of gliomas associated with vascular endothelial growth factor expression. Br J Cancer, 2000. 82(12): p. 1967-73.

Tam, et al., Characterization of genetically altered, interleukin 2-independent natural killer cell lines suitable for adoptive cellular immunotherapy. Hum Gene Ther 10, 1359-1373 (1999).

Tanaka, H., et al., Studies on leukemic cell tissue factor. Thromb Res, 1989. 53(6): p. 535-49.

Tanaka, M. and H. Yamanishi, The expression of tissue factor antigen and activity on the surface of leukemic cells. Leuk Res, 1993. 17(2): p. 103-11.

Tanaka, M. and T. Kishi, Induction of tissue factor by interleukin-2 in acute myelogenous leukemia (AML) cells. Growth Factors, 1990. 4(1): p. 1-8.

Tanaka, M., Induction of tissue factor-like activity of human monoblastic leukemia cell line by tumor necrosis factor-alpha. Thromb Res, 1989. 56(2): p. 201-11.

Tang, Y., et al., Mapping of angiogenic markers for targeting of vectors to tumor vascular endothelial cells. Cancer Gene Ther, 2007. 14(4): p. 346-53.

Tatsumi, K. and N. Mackman, Tissue Factor and Atherothrombosis. J Atheroscler Thromb, 2015. 22(6): p. 543-9.

Tezel, T.H., et al., Targeting tissue factor for immunotherapy of choroidal neovascularization by intravitreal delivery of factor VII-Fc chimeric antibody. Ocul Immunol Inflamm, 2007. 15(1): p. 3-10.

Tolstoshev, Paul, and W. French Anderson. Gene expression using retroviral vectors. Current opinion in biotechnology 1.1 (1990): 55-61.

Ueno, T., et al., Tissue factor expression in breast cancer tissues: its correlation with prognosis and plasma concentration. Br J Cancer, 2000. 83(2): p. 164-70.

Uno, K., et al., Tissue factor expression as a possible determinant of thromboembolism in ovarian cancer. Br J Cancer, 2007. 96(2): p. 290-5.

Versteeg, et al., Tissue factor and cancer metastasis: the role of intracellular and extracellular signaling pathways. Mol Med 10, 6-11 (2004).

Vidal SJ, Rodriguez-Bravo V, Galsky M, Cordon-Cardo C and Domingo-Domenech J. Targeting cancer stem cells to suppress acquired chemotherapy resistance. Oncogene. 2014; 33(36):4451-4463.

Viles-Gonzalez, J.F. and J.J. Badimon, Atherothrombosis: the role of tissue factor. Int J Biochem Cell Biol, 2004. 36(1): p. 25-30.

Wada, H., Y. Wakita, and H. Shiku, Tissue factor expression in endothelial cells in health and disease. Blood Coagul Fibrinolysis, 1995. 6 Suppl 1: p. S26-31.

Wang, B., et al., Radiotherapy of human xenograft NSCLC tumors in nude mice with a 90Y-labeled anti-tissue factor antibody. Cancer Biother Radiopharm, 2005. 20(3): p. 300-9.

Waxman, et al., Tissue factor and its extracellular soluble domain: the relationship between intermolecular association with factor VIIa and enzymatic activity of the complex. Biochemistry 31, 3998-4003 (1992).

Williams, R.O., M. Feldmann, and R.N. Maini, Anti-tumor necrosis factor ameliorates joint disease in murine collagen-induced arthritis. Proc Natl Acad Sci U S A, 1992. 89(20): p. 9784-8.

Wolff, Jon A., et al. "Direct gene transfer into mouse muscle in vivo." Science 247.4949 (1990): 1465-1468.

Wu, George Y., and Catherine H. Wu. "Receptor-mediated gene delivery and expression in vivo." Journal of Biological Chemistry 263.29 (1988): 14621-14624.

Wu, Catherine H., James M. Wilson, and G. Y. Wu. "Targeting genes: delivery and persistent expression of a foreign gene driven by mammalian regulatory elements in vivo." Journal of Biological Chemistry 264.29 (1989): 16985-16987.

Xu, Licheng, et al. Correction of the enzyme deficiency in hematopoietic cells of Gaucher patients using a clinically acceptable retroviral supernatant transduction protocol. N. (1994) Exp. Hemat. 22:223-230.

Yoshida, How to eliminate MYCN-positive hepatic cancer stem cells to prevent the recurrence? Proceedings of the National Academy of Sciences of the United States of America 115, E6388-E6389 (2018).

Zhang, Y., et al., Intravenous somatic gene transfer with antisense tissue factor restores blood flow by reducing tumor necrosis factor-induced tissue factor expression and fibrin deposition in mouse meth-A sarcoma. J Clin Invest, 1996. 97(10): p. 2213-24.

Zhang, Y.M., et al., Vascular origin of Kaposi's sarcoma. Expression of leukocyte adhesion molecule-1, thrombomodulin, and tissue factor. Am J Pathol, 1994. 144(1): p. 51-9.

International Preliminary Report on Patentability issued for Application No. PCT/US2018/051344, dated Apr. 9, 2020.

Office Action and English summary for Japanese Application No. 2020-517592 dated Aug. 23, 2022.

Zhang et al., Pathological expression of tissue factor confers promising antitumor response to a novel therapeutic antibody SC1 in triple negative breast cancer and pancreatic adenocarcinoma, Oncotarget (2017) vol. 8, No. 35, pp. 59086-59102.

Chinese National Intellectual Property Office. Office Acton issued in CN Application No. 201880062881.6 on Jan. 19, 2023. 15 pages including translation.

Japanese Patent Office. Office Action issued in JP Application No. 2020-517592 on Feb. 21, 2023. 11 pages including translation.

Chinese Intellectual Property Office. Office Action issued in Chinese Application No. 2023120701713110 on Dec. 7, 2023. 12 pages, including translation.

Office Action issued for Chinese Application No. 201880062881.6, dated Jul. 14, 2023.

Examination report issued for Australian Application No. 2018341227, dated Sep. 21, 2023.

European Patent Office. Office Action issued in European Application No. 18860547.1 on Nov. 28, 2023. 7 pages.

(56)          References Cited

OTHER PUBLICATIONS

Sadelain M. et al. The promise and potential pitfalls of chimeric antigen receptors. Current opinion in immunology. Apr. 1, 2009;21(2):215-23.

Australian Intellectual Property Office. Examination Report No. 2. Issued in AU Application No. 2018341227 on Aug. 30, 2024. 4 pages.

Australian Intellectual Property Office. Notice of Acceptance. Issued in AU Application No. 2018341227 on Sep. 16, 2024. 4 pages.

Canadian Intelletual Property Office. Office Action issued in CA application No. 3076817 on Oct. 3, 2024. 4 pages.

Chinese National Intellectual Property Administration. Office Action issued in Chinese Application No. 201880062881.6 on Mar. 27, 2024. 13 pages.

Chinese National Intellectual Property Administration. Office Action issued in Chinese Application No. 201880062881.6 on Dec. 7, 2023. 12 pages.

European Patent Office. Communication pursuant to Article 94(3) EPC. Issued in European Application No. 18860547.1 on Aug. 8, 2024. 6 pages.

Uherek et al., "Retargeting of natural killer—cell cytolytic activity to ErbB2-expressing cancer cells results in efficient and selective tumor cell destruction" Blood 2002, 100: 1265-1273.

Mehta RS & Rezvani K. "Chimeric Antigen Receptor expressing Natural Killer Cells for the immunotherapy of Cancer" Frontiers in Immunolology. 2018.

Database USPTO Proteins: "Sequence 598 from U.S. Pat. No. 9,758,776," [Online], Feb. 11, 2018, Database Accession No. AVA78654,. Retrieved from EBI accession No. USPOP: AVA78654.

Office Action for Japanese Application No. 2020-517592, dated Jun. 17, 2025, 20 Pages.

* cited by examiner a. CAR1 Monomer
(1300 bp)
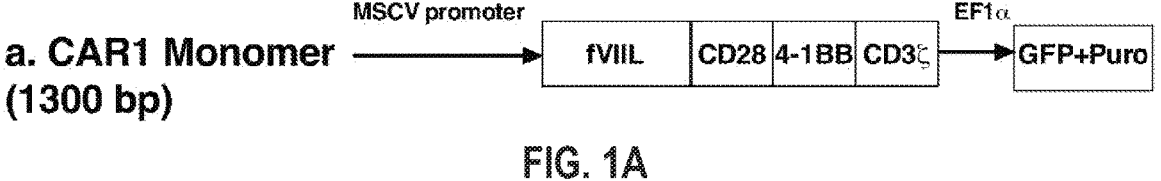
FIG. 1A
b. CAR1 Dimer
(1354 bp)
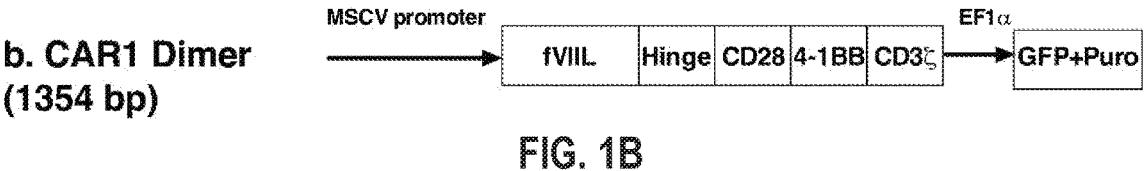
FIG. 1B
CAR1 monomer                    CAR1 dimer
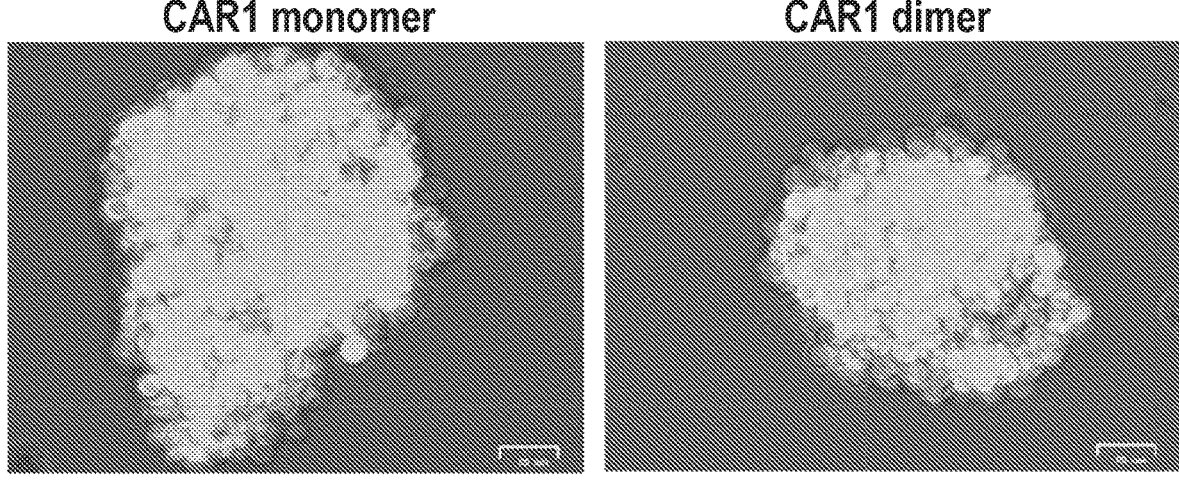
FIG. 2A                         FIG. 2B

UNINFECTED CONTROL

FIG. 4A                 FIG. 4B

SEQUENCE LISTING

```
<160> NUMBER OF SEQ ID NOS: 4

<210> SEQ ID NO 1
<211> LENGTH: 1300
<212> TYPE: DNA
<213> ORGANISM: Artificial Sequence
<220> FEATURE:
<223> OTHER INFORMATION: Synthetic Construct

<400> SEQUENCE: 1
gctagcgcca ccatggtctc ccaggccctc aggctcctct gccttctgct tgggcttcag        60
ggctgcctgg ctgcagtctt cgtaacccag gaggaagccc acggcgtcct gcaccggcgc       120
cggcgcgcca acgcgttcct ggaggagctg cggccgggct ccctggagag ggagtgcaag       180
gaggagcagt gctccttcga ggaggcccgg gagatcttca aggacgcgga gaggacgaag       240
ctgttctgga tttcttacag tgatggtgac cagtgtgcct caagtccatg ccagaatggg       300
ggctcctgca aggaccagct ccagtcctat atctgcttct gcctccctgc cttcgagggc       360
cggaactgtg agacgcacaa ggatgaccag ctgatctgtg tgaacgagaa cggcggctgt       420
gagcagtact gcagtgacca cacgggcacc aagcgctcct gtcggtgcca cgaggggtac       480
tctctgctgg cagacggggt gtcctgcaca cccacagttg aatatccatg tggaaaaata       540
cctattctag aaaaaagaaa tgccagcaag ccccaagggc gaggatcctt ttgggtgctg       600
gtggtggttg gtggagtcct ggcttgctat agcttgctag taacagtggc ctttattatt       660
ttctgggtga ggagtaagag gagcaggctc ctgcacagtg actacatgaa catgactccc       720
cgccgccccg ggcccacccg caagcattac cagccctatg ccccaccacg cgacttcgca       780
gcctatcgct ccttcgaacg tttctctgtt gttaaacggg gcagaaagaa actcctgtat       840
atattcaaac aaccatttat gagaccagta caaactactc aagaggaaga tggctgtagc       900
tgccgatttc cagaagaaga agaaggagga tgtgaactgg aattcagagt gaagttcagc       960
aggagcgcag acgcccccgc gtaccagcag ggccagaacc agctctataa cgagctcaat      1020
ctaggacgaa gagaggagta cgatgttttg gacaagagac gtggccggga ccctgagatg      1080
gggggaaagc cgagaaggaa gaaccctcag gaaggcctgt acaatgaact gcagaaagat      1140
aagatggcgg aggcctacag tgagattggg atgaaaggcg agcgccggag gggcaagggg      1200
cacgatggcc tttaccaggg tctcagtaca gccaccaagg acacctacga cgcccttcac      1260
atgcaggccc tgccccctcg ctgagtttaa acgcggccgc                            1300

<210> SEQ ID NO 2
<211> LENGTH: 1354
<212> TYPE: DNA
<213> ORGANISM: Artificial Sequence
<220> FEATURE:
<223> OTHER INFORMATION: Synthetic Construct

<400> SEQUENCE: 2
```

-continued

```
gctagcgcca ccatggtctc ccaggccctc aggctcctct gccttctgct tgggcttcag        60
ggctgcctgg ctgcagtctt cgtaacccag gaggaagccc acggcgtcct gcaccggcgc       120
cggcgcgcca acgcgttcct ggaggagctg cggccgggct ccctggagag ggagtgcaag       180
gaggagcagt gctccttcga ggaggcccgg gagatcttca aggacgcgga gaggacgaag       240
ctgttctgga tttcttacag tgatggtgac cagtgtgcct caagtccatg ccagaatggg       300
ggctcctgca aggaccagct ccagtcctat atctgcttct gcctccctgc cttcgagggc       360
cggaactgtg agacgcacaa ggatgaccag ctgatctgtg tgaacgagaa cggcggctgt       420
gagcagtact gcagtgacca cacgggcacc aagcgctcct gtcggtgcca cgaggggtac       480
tctctgctgg cagacggggt gtcctgcaca cccacagttg aatatccatg tggaaaaata       540
cctattctag aaaaaagaaa tgccagcaag ccccaagggc gaggatccgc agagcccaaa       600
tcttgtgaca aaactcacac atgcccaccg tgcccaggat ccttttgggt gctggtggtg       660
gttggtggag tcctggcttg ctatagcttg ctagtaacag tggcctttat tattttctgg       720
gtgaggagta gaggagcag gctcctgcac agtgactaca tgaacatgac tccccgccgc        780
cccgggccca cccgcaagca ttaccagccc tatgccccac cacgcgactt cgcagcctat       840
cgctccttcg aacgtttctc tgttgttaaa cggggcagaa agaaactcct gtatatattc       900
aaacaaccat ttatgagacc agtacaaact actcaagagg aagatggctg tagctgccga       960
tttccagaag aagaagaagg aggatgtgaa ctggaattca gagtgaagtt cagcaggagc      1020
gcagacgccc ccgcgtacca gcagggccag aaccagctct ataacgagct caatctagga      1080
cgaagagagg agtacgatgt tttggacaag agacgtggcc gggaccctga gatggggga       1140 aagccgagaa ggaagaaccc tcaggaaggc ctgtacaatg aactgcagaa agataagatg      1200
gcggaggcct acagtgagat tgggatgaaa ggcgagcgcc ggagggggcaa ggggcacgat      1260 ggcctttacc agggtctcag tacagccacc aaggacacct acgacgccct tcacatgcag      1320
gccctgcccc ctcgctgagt ttaaacgcgg ccgc                                  1354
```

```
<210> SEQ ID NO 3
<211> LENGTH: 570
<212> TYPE: DNA
<213> ORGANISM: Artificial Sequence
<220> FEATURE:
<223> OTHER INFORMATION: Synthetic Construct

<400> SEQUENCE: 3
atggtctccc aggccctcag gctcctctgc cttctgcttg ggcttcaggg ctgcctggct        60
gcagtcttcg taacccagga ggaagcccac ggcgtcctgc accggcgccg cgcgccaac       120 gcgttcctgg aggagctgcg gccgggctcc ctggagaggg agtgcaagga ggagcagtgc       180
tccttcgagg aggcccggga gatcttcaag gacgcggaga ggacgaagct gttctggatt       240
tcttacagtg atggtgacca gtgtgcctca agtccatgcc agaatggggg ctcctgcaag       300
gaccagctcc agtcctatat ctgcttctgc ctccctgcct cgagggccg gaactgtgag        360 acgcacaagg atgaccagct gatctgtgtg aacgagaacg cggctgtga gcagtactgc        420 agtgaccaca cgggcaccaa gcgctcctgt cggtgccacg aggggtactc tctgctggca       480
gacggggtgt cctgcacacc cacagttgaa tatccatgtg aaaaatacc tattctagaa        540 aaaagaaatg ccagcaagcc ccaagggcga                                         570
```

```
<210> SEQ ID NO 4
<211> LENGTH: 190
```

-continued

```
<212> TYPE: PRT
<213> ORGANISM: Artificial Sequence
<220> FEATURE:
<223> OTHER INFORMATION: Synthetic Construct

<400> SEQUENCE: 4

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
            85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
            165                 170                 175

Pro Ile Leu Glu Lys Arg Asn Ala Ser Lys Pro Gln Gly Arg
            180                 185                 190
```

TISSUE FACTOR-TARGETING CAR-NK AND CAR-T CELL THERAPY

CROSS-REFERENCE TO RELATED APPLICATIONS

This application is a national stage application filed under 35 U.S.C. § 371 of PCT/US2018/051344 filed Sep. 17, 2018, which claims benefit of U.S. Provisional Application No. 62/564,006, filed Sep. 27, 2017, incorporated herein by reference in its entirety.

BACKGROUND

Tissue factor ("TF") is a transmembrane glycoprotein that is the major initiator of the coagulation cascade. Under normal physiological conditions, active TF is not in contact with blood. During vascular injury, exposure to blood of sub-endothelial TF and collagen leads to activation of coagulation factors and platelets and subsequently to hemostatic plug formation. The inappropriate induction of TF expression in a variety of clinical settings can lead to life threatening thrombosis and/or contribute to pathological complications. TF exposure following plaque rupture is believed to be responsible for thrombotic occlusion leading to acute myocardial infarction and stroke. In these settings, proinflammatory signaling pathways activated by coagulation factors also contribute to edema formation and increased infarct size. Vascular injury associated with angioplasty leads to upregulation of TF on smooth muscle cells (SMC), which is believed to induce cell signaling pathways associated with restenosis. TF overexpression in cancer and gram-negative sepsis leads to life threatening thrombosis and activation of inflammatory pathways.

TF is a modulator of pathological angiogenesis. In vivo studies revealed that TF is also a unique pathological angiogenic vascular endothelial cell (VEC)-surface receptor in vivo because of its selective expression on angiogenic VECs in vivo in tumor vasculature (Contrino et al. 1996; Folkman et al. 1996; Hu et al. 1999; Hu et al. 2001; Cheng et al. 2011; Duanmu et al. 2011), ocular (Bora et al. 2003) and endometriotic (Krikun et al. 2010) neovasculature from patients or animal models. Vascular endothelial growth factor (VEGF) plays a central role in angiogenesis-dependent cancer and non-malignant human diseases (Ferrara et al. 2002), such as macular degeneration (Klagsbrun et al. 1987), rheumatoid arthritis (Afuwape et al. 2002) and endometriosis (Fujimoto et al. 1999). Specifically, VEGF stimulates angiogenesis by binding to VEGR receptors on VECs in the pathological neovasculature (usually micro- or capillary vessels) in those angiogenesis-dependent diseases (Hu et al. Angiogenesis 2016). Using VEGF-induced in vitro angiogenic vascular endothelial models, it was shown that TF is an angiogenic-specific receptor and the target for factor VII-targeted therapeutics (Hu et al. Angiogenesis 2016), suggesting that TF-targeting agents can have therapeutic potential to treat cancer (solid cancer and leukemia), wet form of age-related macular degeneration (AMD), endometriosis and rheumatoid arthritis.

TF is a common (yet specific) biomarker and therapeutic target for cancer cells, cancer stem cells (CSC) (Hu et al. Oncotarget 2016) and tumor vascular endothelial cells in solid cancers. TF is highly expressed in these cancer cells (80%-100% in breast cancer, 40%-80% in lung cancer and 84% in ovarian cancer). These three types of cancer are not only difficult to control, but also are major causes of mortality in the United States and worldwide and often develop CSC-based resistance to chemotherapy and radiation therapy (Vidal et al. 2014; Moncharmont et al. 2012; Koch et al. 2010). In addition to the cancer of breast, lung and ovary, TF is also expressed at high percentages in many other human solid cancers, leukemias, sarcomas, myeloma and potentially lymphoma (Table 1), for instance, 95% in primary melanoma and 100% in metastatic melanoma, 53%-90% in pancreatic cancer, 57%-100% in colorectal cancer, 63%-100% in hepatocellular carcinoma, 60%-78% in primary and metastatic prostate cancer and 47%-75% in glioma (Hu. Antibodies 2018). Very recently, it was shown that TF is expressed by cancer stem cells in breast, lung, ovarian cancer and potentially in other solid cancers such as head and neck cancer and TF-targeting agents can eradicate those TF-expressing cancer stem cells without drug resistance (Hu et al. Oncotarget 2016).

It has also been shown that TF is expressed by choroidal neovasculature (CNV), a model of AMD in experimental animals (Bora et al. 2003). It has also been shown that TF was expressed by angiogenic vascular endothelial cells in endometriotic lesions.

The adoptive transfer of chimeric antigen receptor (CAR)-expressing immune effector cells represents a novel cancer immunotherapy approach. The concept of the CAR is based upon the idea of expressing novel receptors on the T or NK cell surface that enable the T and NK cell to identify corresponding antigens on the surface of a target cell. The basic CAR construct consists of an extracellular antigen-recognition domain, usually single-chain antibody variable fragments (scFv), attached to an extracellular spacer domain, a trans-membrane domain of CD28 and a signaling cytoplasmic domain such as 4-1BB (CD137), OX40 (CD134), DAP10, ICOS and CD3zeta chain (CD3ζ). The most advanced application is the use of CAR-T cells targeting CD19, a surface antigen on B cell malignancies, which has demonstrated antitumor efficacy in patients with B cell malignancies (P. J. Paszkiewicz et al., Targeted antibody-mediated depletion of murine CD19 CAR T cells permanently reverses B cell aplasia. J Clin Invest 126, 4262-4272 (2016)). What is needed in the art are TF-targeting CAR-modified immune effector cells.

BRIEF DESCRIPTION OF THE FIGURES

The accompanying figures, which are incorporated in and constitute a part of this specification, illustrate several aspects of the disclosure, and together with the description, serve to explain the principles of the disclosure.

FIGS. 1A-B show a diagram of TF-targeting CAR1 monomer (FIG. 1A) and dimer (FIG. 1B). fVIIL: Factor VII light chain. Hinge: Hinge region of human IgG1. GFP: Green fluorescence protein. Puro: Puromycin. The only difference between CAR1 monomer and dimer is that the dimer construct contains an IgG1 hinge region, in which two cysteine residues will form disulfide bonds to form a homologous dimer.

FIGS. 2A-C show generation of stable TF-targeting CAR1-NK cell lines. Lentivirus encoding CAR1 monomer and dimer have successfully transfected NK92MI/full length CD16 (fCD16) cell line and stable cell lines have been generated under selection of 2.5 µg/ml puromycin (FIGS. 2a & b). Uninfected NK92MI/fCD16 cells were used as control and did not express GFP (FIG. 2c). Photos were taken using bright and green channels and were merged under Zeo Cell Imager (Bio-Rad). Scale bars: 100 µm.

FIGS. 4A-D show expression of CAR1, CD16 and beta actin in NK92MI/fCD16 cells by RT-PCR. Total RNA was extracted by Trizol reagents from NK92MI/fCD16 cells stably transfected with CAR1 monomer (M) or dimer (D). Parental NK92MI cells that were not transfected with CD16 plasmid were used as a negative control (C) for CAR1 and CD16. A. CAR1. B. CD16. C. Beta actin was assayed as a loading control for total RNAs. Representative photos from two independent experiments. D. ELISA assay for fVII expression using anti-human factor VII HRPO conjugate (Cedarlane Laboratories). Data in D were presented as mean +/−SEM.

DETAILED DESCRIPTION

Definitions

Figure 2C:
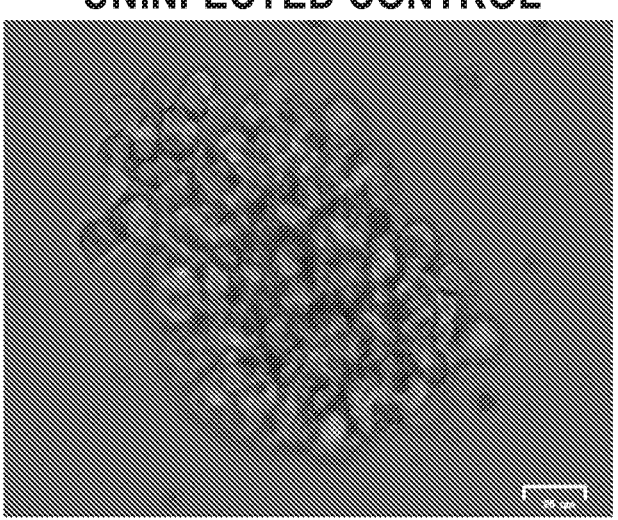

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +−0.20% or +−0.10%, more preferably +−0.5%, even more preferably +−0.1%, and still more preferably +−0.0.1% from the specified value, as such variations are appropriate to perform the disclosed methods.

A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

An "analogue," "analog" or "derivative," which are used interchangeably, refers to a compound, e.g., a peptide or polypeptide, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, small-hairpin RNA (shRNA), ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

As used herein, the term "diagnosis" refers to the determination of the presence of a disease or disorder. In some embodiments of the present invention, methods for making a diagnosis are provided which permit determination of the presence of a particular disease or disorder.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

General

Disclosed herein are Tissue Factor (TF)-targeting CAR-NK and CAR-T cells. In the design and development of TF-targeting CAR, the full length (wild type and active site mutated) or the light chain of factor VII (fVII or fVIIL) is used, the natural ligand for TF, instead of antibody or scFv against TF, as recognition domain for TF. First, affinity for fVII to TF is about 100-1000 fold greater than antibody to TF antigen. Second, fVII can be synthesized by recombinant DNA technology without need of humanization for monoclonal antibodies or screening scFv libraries. Furthermore, the light chain of fVII (the first 152 amino acid residues) can bind equally or stronger than full-length fVII to TF-expressing human and murine cancer cells (Hu et al. *Cancer Immunology Research*. 2018). Thus, the TF-targeting CAR disclosed herein consists of human factor VII light chain as TF-targeting domain, without or with a hinge region of human IgG1, attached to CD28 transmembrane and cytoplasmic domains and followed by cytoplasmic domains of 4-1BB and CD3ζ (FIG. 1), named TF-targeting CAR1 monomer and dimer (GenBank accession #MF806378 and MF806379, respectively).

Any TF-targeting/binding molecule can be used with the compositions and methods disclosed herein to target TF in vivo or in vitro. As mentioned above, fVII can be used to target TF. Any fVII capable of targeting TF is therefore disclosed herein. The fVII can be obtained from any subject, including but not limited to humans, primates, murine species, bovine, porcine, rat, canine, and feline species. An example can be found in SEQ ID NO: 4 (the nucleic acid encoding the polypeptide is represented by SEQ ID NO: 3). Disclosed herein is an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to SEQ ID NO: 4.

In certain non-limiting embodiments, the transmembrane domain of the CAR can comprise a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, or a synthetic peptide (not based on a protein associated with the immune response), or a combination thereof.

In certain non-limiting embodiments, an intracellular domain of the CAR further comprises at least one signaling region. The at least one signaling region can include a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. In certain embodiments, the signaling region is a co-stimulatory signaling region. In certain embodiments, the co-stimulatory region comprises at least one co-stimulatory molecule, which can provide optimal lymphocyte activation.

As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR+ T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID NO: 15, the nucleotide sequence encoding ICOS is set forth in SEQ ID NO: 16, and the nucleotide sequence encoding DAP-10 is set forth in SEQ ID NO: 17 in U.S. Pat. No. 7,446,190), which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules: CD28 and 4-1BB or CD28 and OX40.

In certain embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

Cells Expressing TF-Targeting CAR

The presently disclosed subject matter provides immune-responsive cells expressing a CAR that comprises TF binding domain, as described above. The immunoresponsive cells can be transduced with a presently disclosed CAR such that the cells express the CAR. The presently disclosed subject matter also provides methods of using such cells for the treatment of cancer, such as triple-negative breast cancer (TNBC). The immunoresponsive cells of the presently disclosed subject matter can be cells of the lymphoid lineage, which can be primary cells or ex vivo activated and expanded cells from healthy donors and/or from patients. The cells can be obtained from any source known to those of skill in the art. The lymphoid lineage, comprising B, T and natural killer (NK) cells, provides for the production of antibodies, regulation of the cellular immune system, detection of foreign agents in the blood, detection of cells foreign to the host, and the like.

Non-limiting examples of immunoresponsive cells of the lymphoid lineage include T cells, Natural Killer (NK) cells, cytotoxic T lymphocytes (CTLs), regulatory T cells, embryonic stem cells, and pluripotent stem cells {e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., TEM cells and TEMRA cells), Regulatory T cells (also known as suppressor T cells), Natural killer T cells, Mucosal associated invariant T cells, and γδ T cells. In certain embodiments, the CAR-expressing T cells express Foxp3 to achieve and maintain a T regulatory phenotype. Natural killer (NK) cells can be lymphocytes that are part of cell-mediated immunity and act during the innate immune response. NK cells do not require prior activation in order to perform their cytotoxic effect on target cells. Cytotoxic T cells (CTL or killer T cells) are a subset of T lymphocytes capable of inducing the death of infected somatic or tumor cells.

The immunoresponsive cells of the presently disclosed subject matter can express a TF-binding domain. Such immunoresponsive cells can be administered to a subject (e.g., a human subject) in need thereof for the treatment of TF-related disorders, such as cancer. In certain embodiments, the immunoresponsive cell is a T cell. The T cell can be a CD4+ T cell or a CD8+ T cell. In certain embodiments, the T cell is a CD4+ T cell. In another embodiment, the T cell is a CD8+ T cell.

A presently disclosed immunoresponsive cell can be further transduced with at least one co-stimulatory ligand, such that the immunoresponsive cell co-expresses or is induced to co-express the TF-specific CAR and the at least one co-stimulatory ligand. The interaction between the TF-specific CAR and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus)

containing a short cytoplasmic segment and a relatively long extracellular region. TNF superfamily members include, without limitation, nerve growth factor (NGF), CD40L (CD40L)/CD154, CD137L/4-1BBL, TNF–, CD134L/OX40L/CD252, CD27L/CD70, Fas ligand (FasL), CD30L/CD153, tumor necrosis factor beta (TNFP)/lymphotoxin-alpha (LTcc), lymphotoxin-beta (LTP), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins, in that they possess an immunoglobulin domain (fold). Immunoglobulin superfamily ligands include, but are not limited to, CD80 and CD86, both ligands for CD28, PD-L1/(B7-H1) that ligands for PD-1.

In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell is transduced with one co-stimulatory ligand that is 4-1BBL. In certain embodiments, the immunoresponsive cell is transduced with two co-stimulatory ligands that are 4-1BBL and CD80. CARs transduced with at least one co-stimulatory ligand are described in U.S. Pat. No. 8,389,282, which is incorporated by reference in its entirety.

Furthermore, a presently disclosed immunoresponsive cell can be further transduced with at least one cytokine, such that the immunoresponsive cell secretes the at least one cytokine as well as expresses the TF-specific CAR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The TF-specific or TF-targeted human lymphocytes that can be used in peripheral donor lymphocytes, e.g., those disclosed in Sadelain, M., et al. 2003 Nat Rev Cancer 3:35-45 (disclosing peripheral donor lymphocytes genetically modified to express CARs), in Morgan, R. A., et al. 2006 Science 314: 126-129 (disclosing peripheral donor lymphocytes genetically modified to express a full-length tumor antigen-recognizing T cell receptor complex comprising the α and β heterodimer), in Panelli, M. C., et al. 2000 J Immunol 164:495-504; Panelli, M. C., et al. 2000 J Immunol 164:4382-4392 (disclosing lymphocyte cultures derived from tumor infiltrating lymphocytes (TILs) in tumor biopsies), and in Dupont, J., et al. 2005 Cancer Res 65:5417-5427; Papanicolaou, G. A., et al. 2003 Blood 102:2498-2505 (disclosing selectively in vitro-expanded antigen-specific peripheral blood leukocytes employing artificial antigen-presenting cells (AAPCs) or pulsed dendritic cells). The immunoresponsive cells {e.g., T cells) can be autologous, non-autologous {e.g., allogeneic), or derived in vitro from engineered progenitor or stem cells.

In certain embodiments, a presently disclosed immunoresponsive cell {e.g., T cell) expresses from about 1 to about 4, from about 2 to about 4, from about 3 to about 4, from about 1 to about 2, from about 1 to about 3, or from about 2 to about 3 vector copy numbers/cell of a presently disclosed TF-specific CAR.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

Vectors

Genetic modification of immunoresponsive cells (e.g., T cells, CTL cells, NK cells) can be accomplished by transducing a substantially homogeneous cell composition with a recombinant DNA or RNA construct. The vector can be a retroviral (Liu et al., Leukemia 2018) or lentiviral (Mehta and Rezvani, Front Immunol 2018; Nowakowska et al., Cancer Immunol Immunother 2018) vector (e.g., gamma retroviral), which is employed for the introduction of the DNA or RNA construct into the host cell genome. Similar to lentiviral vectors as described in FIGS. 1-4, for example, a polynucleotide encoding the TF-specific CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA), non-viral Sleeping Beauty transposon or mRNA transfection (Hu et al., Acta Pharmacol Sin 2018; Mehta and Rezvani, Front Immunol 2018) can be used.

For initial genetic modification of the cells to provide TF-specific CAR expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) Blood 80: 1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89: 1817.

Transducing viral vectors can be used to express a co-stimulatory ligand (e.g., 4-1BBL and IL-12) in an immuno-responsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263 267, 1996; and Miyoshi et al., Proc. Natl. Acad. Sci. U.S.A. 94: 10319, 1997). Other viral vectors that can be used include, for example, adeno-viral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244: 1275-1281, 1989; Eglitis et al, BioTechniques 6:608-614, 1988; Tolstoshev et al., Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Nat'l. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263: 14621, 1988; Wu et al., Journal of Biological Chemistry 264: 16985, 1989), or by micro-injection under surgical conditions (Wolff et al., Science 247: 1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation. cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1 a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Sequences: Homology/Alteration/Optimization

The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity with all or part of a naturally-occurring amino, acid sequence of the presently disclosed subject matter. The length of sequence comparison is at least 5, 10, 15, 20, 25, 50, 75, 100 or more amino acid residues. Again, in an exemplary approach to determining the degree of identity, a BLAST program may be used, with a probability score between e"3 and e"100 indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least 5, 10, 13, or 15 amino acids. In certain embodiments, a fragment is at least 20 contiguous amino acids, at least 30 contiguous amino acids, or at least 50 contiguous amino acids. In certain embodiments, a fragment is at least 60 to 80, 100, 200, 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an antigen-binding domain that specifically binds to TF can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various ds-elements in transcription and translation. Any suitable codon optimization methods or technologies that are known to ones skilled in the art can be used to modify the polynucleotides of the presently disclosed subject matter, including, but not limited to, OPTIMUM-GENE™, Encor optimization, and Blue Heron.

The amino acids used to create the CARs disclosed herein can be substituted with other amino acids, as long as they retain their functional ability to be recognized by Tissue Factor (TF). Substitutional or replacement variants typically contain the exchange of one amino acid for another at one or more sites within the polypeptide and may be designed to modulate one or more properties of the polypeptide, particularly its effector functions and/or bioavailability. Certain specific amino acid exchanges in chimeric polypeptides of the embodiments are detailed above. Further substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, a modified polypeptide may possess an insertion of residues, which typically involves the addition of at least one residue in the polypeptide. This may include the insertion of a targeting polypeptide or simply a single residue. Terminal additions, called fusion proteins, are discussed below.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Treatment/Therapy Methods

CAR-T and -NK cell therapy has been evaluated in hematological malignancies in clinical trials and in approved clinical applications (Luskin et al. Chimeric Antigen Receptor Therapy in Acute Lymphoblastic Leukemia Clinical Practice. Curr Hematol Malig Rep, 2017) and is also being translated into solid cancers (Morello et al. Mesothelin-Targeted CARs: Driving T Cells to Solid Tumors. Cancer Discov, 2016. 6(2): p. 133-46). This strategy not only provides systemic immunity that is required for effective cancer immunotherapy (Spitzer, M. H., et al., Systemic Immunity Is Required for Effective Cancer Immunotherapy. Cell, 2017. 168(3): p. 487-502 e15) but can also increase local infiltration of T and NK cells in tumor microenvironment. In line with this idea, checkpoint inhibitors and CAR-T cells can be used in multiple myeloma (Gay, F., et al., Immuno-oncologic Approaches: CAR-T Cells and Checkpoint Inhibitors. Clin Lymphoma Myeloma Leuk, 2017. 17(8): p. 471-478). As such, multiple myeloma can be used to test the idea of the combination therapy of checkpoint blockades with CAR-T therapy to increase infiltration of T cells in tumor microenvironment to overcome the resistance and thus to optimize the efficacy of immune checkpoint blockade therapy. To increase local infiltration of CAR-T and -NK cells, CAR-T or -NK cells can be delivered locally or regionally, such as intracranial delivery for brain cancer and intra-hepatical infusion for hepatocellular carcinoma and liver metastases from primary colorectal cancer (Sridhar, P. and F. Petrocca, Regional Delivery of Chimeric Antigen Receptor (CAR) T-Cells for Cancer Therapy. Cancers (Basel), 2017. 9(7)). Cell therapy, including ex vivo expanded and activated NK cells, can be used for hematological cancers as well as for solid cancers (Baggio, L., et al., Natural killer cell adoptive immunotherapy: Corning of age. Clin Immunol, 2017. 177: p. 3-11.) To increase homing of the systemically infused NK cells to tumor microenvironment, it has been reported (Kremer, V., et al., Genetic engineering of human NK cells to express CXCR2 improves migration to renal cell carcinoma. J Immunother Cancer, 2017, 5(1): p. 73) that genetic engineering of human NK cells to express a chemokine receptor CXCR2 improved migration to renal cell carcinoma that expresses the ligand for CXCR2.

The fVII-CAR modified immune effector cells as described herein can be used to treat a variety of diseases and disorders. In fact, any disease or disorder associated with Tissue Factor (TF) can be treated with the cells disclosed herein. Pathological angiogenesis, the formation of neovasculature, is involved in many clinic significant human diseases, notably cancer, age-related macular degeneration (AMD), endometriosis and rheumatoid arthritis (RA) (Hu. Antibodies 2018). Macrophage is involved in the progression of many human diseases, such as atherosclerosis and viral infections (HIV and Ebola) (Hu. Antibodies 2018). TF may be selectively expressed on angiogenic vascular endothelial cells (VECs) in these pathological angiogenesis-dependent human diseases and on disease-associated macrophages. Under physiology condition, TF is not expressed by quiescent VECs and monocytes, but is solely restricted on some cells (such as pericytes) that are located outside the blood circulation and inner layer of blood vessel walls. In cancer, for example, the cancer cells also overexpress TF in many types of solid cancers, leukemia (AML and ALL) and sarcoma. Moreover, TF is also expressed by cancer-initiating stem cells (CSCs) and can serve as a novel oncotarget for eradication of CSCs without drug resistance. Therefore, examples of diseases that can be treated by the methods disclosed herein include, but are not limited to, pathological neovasculature of cancer, age-related macular degeneration and endometriosis, leukemia and lymphoma, solid tumors, rheumatoid arthritis, atherosclerosis, and viruses, including HIV and Ebola. A list of cancers associated with TF can be found in Table 1.

Administration

TF-specific CARs and immunoresponsive cells expressing thereof of the presently disclosed subject matter can be provided systemically or directly to a subject for treating or preventing a disease associated with TF. In certain embodiments, the TF-specific CARs and immunoresponsive cells expressing thereof are directly injected into an organ of interest (e.g., an organ affected by cancer). Alternatively or additionally, the TF-specific CARs and immunoresponsive cells expressing thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

TF-specific CARs and immunoresponsive cells expressing thereof of the presently disclosed subject matter can be administered in any physiologically acceptable vehicle. Usually, at least $1\times10^5$ cells can be administered, eventually reaching $1\times10^{10}$ or more. A cell population comprising immunoresponsive cells expressing a TF-specific CAR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells expressing a TF-specific CAR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, IL-27, as well as the other interleukins, the colony stimulating factors, such as G-, M- and GM-CSF, interferons, e.g., γ-interferon.

Compositions of the presently disclosed subject matter comprise pharmaceutical compositions comprising immunoresponsive cells expressing a TF-specific CAR and a pharmaceutically acceptable carrier. Administration can be autologous or non-autologous. For example, immunoresponsive cells expressing a TF-specific CAR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells expressing a TF-specific CAR), it can be formulated in a unit dosage injectable form (solution, suspension, emulsion).

Formulations

Immunoresponsive cells expressing a generally TF-specific CAR and compositions comprising thereof of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions comprising immunoresponsive cells expressing a generally TF-specific CAR of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the present invention, however, any vehicle, diluent, or additive used would have to be compatible with the immunoresponsive cells expressing a generally TF-specific CAR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

In summary, fVII-CAR modified immune effector cells can be administered to a subject in need thereof. Administration may be local or systemic, depending upon the type of pathological condition involved in the therapy. Administration can be via any method known in the art such as, for example, intravenous, intraperitoneal, intrahepatic, intramuscular, intratumoral, subcutaneous, intrasynovial, intraocular, intraplaque, intracranial, or intradermal injection of the fVII-CAR modified immune effector cells.

The amount of fVII-CAR modified immune effector cells necessary to bring about the therapeutic treatment is not fixed per se, and necessarily is dependent on the concentration of ingredients in the composition administered in conjunction with a pharmaceutical carrier, adjunct compounds in the composition administered that enhance the immune system response more fully illustrated below, and the age, weight, and clinical condition of the patient to be treated. Preferred compositions deliver the modified cells in effective amounts without producing unacceptable toxicity to the patient.

Pharmaceutical compositions or formulations of the invention may also include other carriers, adjuvants, stabilizers, preservatives, dispersing agents, and other agents conventional in the art having regard to the type of formulation in question.

Kits

The presently disclosed subject matter provides kits for the treatment or prevention of a TF-expressing disease, such as cancer In certain embodiments, the kit comprises a therapeutic or prophylactic composition containing an effective amount of an immunoresponsive cell comprising a TF-specific CAR in unit dosage form. In particular embodiments, the cells further expresses at least one co-stimulatory ligand. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the immunoresponsive cell is provided together with instructions for administering the cell to a subject having or at risk of developing a disease, such as cancer. The instructions will generally include information about the use of the composition for the treatment or prevention of a disease. In other embodiments, the instructions include at least one of the following: description of the therapeutic agent; dosage schedule and administration for treatment or prevention of a disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

Example 1: TF-Targeting CAR Constructs

To efficiently transduce CAR constructs into NK and T cells, the CAR1 dimer and monomer cDNAs (SEQ ID NOS: 1 and 2) were subcloned into the multicloning site (MCS) of pCDH lentivector, which has successfully infected human NK line NK92 (X. Chen et al., A combinational therapy of EGFR-CAR NK cells and oncolytic herpes simplex virus 1 for breast cancer brain metastases. *Oncotarget* 7, 27764-27777 (2016). The cDNA sequences of CAR1 monomer and dimer were confirmed by Sanger DNA sequencing and have been deposited at GenBank (accession #MF806378 and MF806379, SEQ ID NOS: 1 and 2).

Figures 3A, 3B, 3C, 3D, 3E, 3F:
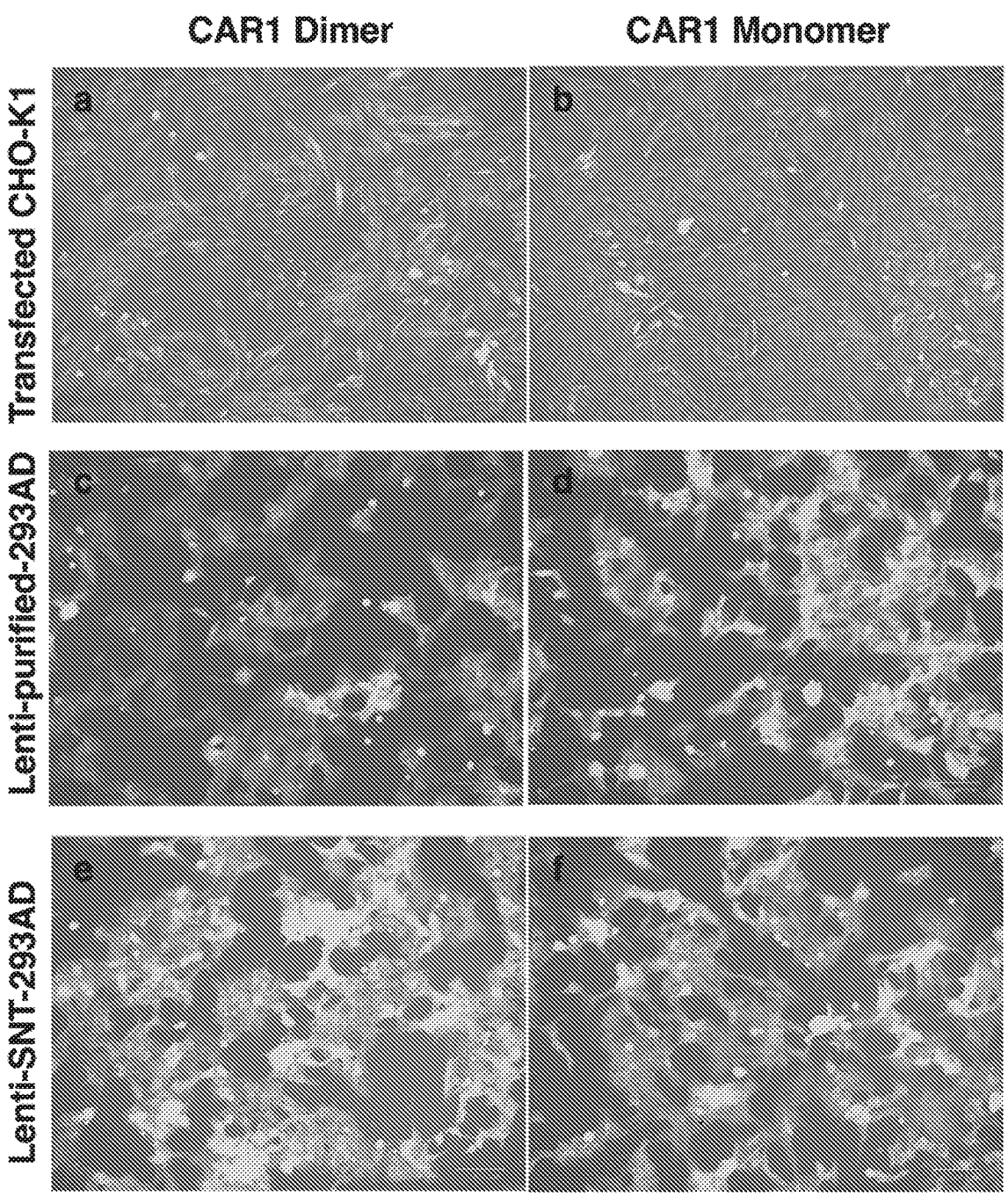
FIGS. 3A-F show plasmid pCDH and lentivirus encoding TF-targeting CAR1 dimer and monomer can transfect Chinese Hamster Ovary cells CHO-K1 (FIG. 3a, 3b) and infect human embryonic kidney cells 293AD, either using PEG-it purified virus (FIG. 3c, 3d) or unpurified vector in supernatant (SNT) (FIG. 3e, 3f). Photos were taken using bright and green channels and were merged under Zeo Cell Imager (Bio-Rad). Scale bars: 100 μm.

To ensure that the pCDH plasmid and lentivirus can lead to CAR1 expression, pCDH plasmid encoding CAR1 (with GFP and Puro) was transfected into CHO-K1 cells, which have been previously transfected with pcDNA3.1(+) plasmid vectors for producing TF-targeting immunoconjugates fVII-IgG1Fc (called ICON) (20-23) and fVIII-IgG1Fc (called L-ICON1, for light chain ICON, as a second generation ICON). 293AD cells were also infected with pCDH-derived lentivirus in supernatant and in PEG-it purified vector. FIG. 3 showed that CHO-K1 cells and 293AD cells all expressed GFP after transfection with pCDH or lentivirus either in SNT or purified vector, indicating mammalian cells (hamster and human origins) can be transfected and infected by lentivirus. Then Lenti-CAR1 dimer and monomer vectors were used to infect NK92MI/fCD16 cells, which have been transfected with plasmid pcDNA3.1(+) encoding full length human CD16, a Fc receptor for IgG1Fc that can mediate antibody-dependent cellular cytotoxicity (ADCC). FIG. 2 showed that NK92MK/fCD16 cells expressed GFP after infection with lenti-CAR1 dimer and monomer, whereas uninfected control cells did not have GFP, indicating that lentivirus has successfully infected the NK cell line. CAR1 expression is tested using anti-human factor VII antibodies in flow cytometry, ELISA and Western-blotting.

Example 2: Tissue Factor-Targeting CAR-NK Cells for Immunotherapy of Triple-Negative Breast Cancer Introduction It was determined that tissue factor (TF) is a novel, common yet selective surface oncotarget for triple-negative breast cancer (TNBC), which is typically an incurable malignancy due to the lack of targeted immunotherapy. To address the unmet need for treatment, disclosed herein is a TF-targeting CAR-NK cells expressing fVIIL-CD28-4-1BB-CD3zeta, with or without a hinge region of human IgG1 (for potential homodimerization) between the extracellular targeting domain (factor VII light chain, fVIIL) and transmembrane domain (CD28) as TF-CAR1 dimer and monomer for CAR-NK immunotherapy of TNBC. Results demonstrate that TF-CAR1-NK cells can kill TNBC cells in vitro and are effective and safe for the treatment of TNBC in cell line-derived and patient's tumor-derived xenograft mouse models.

Triple-negative breast cancer (TNBC) represents nearly 15% of globally diagnosed breast cancer (A. Jemal et al., Global cancer statistics. CA: a cancer journal for clinicians 61, 69-90 (2011); C. K. Anders, L. A. Carey, Biology, metastatic patterns, and treatment of patients with triple-negative breast cancer. Clinical breast cancer 9 Suppl 2, S73-81 (2009); C. A. Hudis, L. Gianni, Triple-negative breast cancer: an unmet medical need. The oncologist 16 Suppl 1, 1-11 (2011)). Due to the lack of validated therapeutic target molecules, TNBC is one of the most difficult to treat malignancies, in most cases is considered an incurable malignancy. There are currently no molecularly targeted therapies approved for TNBC.

TF has been identified as an angiogenesis-specific receptor on VEGF-stimulated angiogenic microvascular endothelial models in vitro as well as in vivo in angiogenic VECs (the inner layer) of the pathological neovasculature of endometriosis, age-related macular degeneration (AMD) and solid cancers, including human melanoma (Z. Hu, Y. Sun, A. Garen, Targeting tumor vasculature endothelial cells and tumor cells for immunotherapy of human melanoma in a mouse xenograft model. Proceedings of the National Academy of Sciences of the United States of America 96, 8161-8166 (1999); Z. Hu, A. Garen, Intratumoral injection of adenoviral vectors encoding tumor-targeted immunoconjugates for cancer immunotherapy. Proceedings of the National Academy of Sciences of the United States of America 97, 9221-9225 (2000)), lung cancer (J. Cheng et al., Effective treatment of human lung cancer by targeting tissue factor with a factor VII-targeted photodynamic therapy. Current cancer drug targets 11, 1069-1081 (2011) and breast cancer (J. Cheng et al., Effective treatment of human lung cancer by targeting tissue factor with a factor VII-targeted photodynamic therapy. Current cancer drug targets 11, 1069-1081 (2011)) from tumor xenografts in mice or breast cancer tissues from patients (J. Contrino, G. Hair, D. L. Kreutzer, F. R. Rickles, In situ detection of tissue factor in vascular endothelial cells: correlation with the malignant phenotype of human breast disease. Nat Med 2, 209-215 (1996). In solid cancers and leukemia, TF is also frequently over-expressed on a variety of solid cancer cells and leukemic cells (Z. Hu, Factor VII-Targeted Photodynamic Therapy for Breast Cancer and Its Therapeutic Potential for Other Solid Cancers and Leukemia, Breast Cancer—Current and Alternative Therapeutic Modalities, Esra Gunduz and Mehmet Gunduz (Ed.), ISBN: 978-953-307-776-5). TF is also a novel oncotarget for cancer stem cells (CSCs) isolated from cancer cell lines, tumor xenografts and cancer patients of breast, lung and ovarian cancer (Z. Hu et al., Targeting tissue factor as a novel therapeutic oncotarget for eradication of cancer stem cells isolated from tumor cell lines, tumor xenografts and patients of breast, lung and ovarian cancer. Oncotarget 8, 1481-1494 (2017)). It has been found that CSCs do not develop resistance to TF-targeting therapy. To identify a targetable surface molecule for TNBC therapy, it was determined that TF is a novel, common yet selective oncotarget on the TNBC cancer cells (up to 85% of patients with TNBC) and tumor vascular endothelial cells (VECs) (Z. Hu et al., Targeting Tissue Factor for Immunotherapy of Triple-Negative Breast Cancer Using a Second-Generation ICON. Cancer Immunol Res 6, 671-684 (2018)). Thus, TF is a common yet specific oncotarget for three major tumor compartments, i.e., cancer cells, tumor angiogenic vascular endothelial cells and cancer stem cells, in several types of solid cancers including TNBC.

The adoptive transfer of chimeric antigen receptor (CAR)-expressing T and natural killer cells represents a novel cancer immunotherapy approach. The concept of the CAR is based upon the idea of expressing novel receptors on the T or NK cell surface that would enable the T and NK cell to identify corresponding antigens on the surface of a target cell. The basic CAR construct consists of an extracellular antigen-recognition domain, usually single-chain antibody variable fragments (scFv), attached to an extracellular spacer domain, a transmembrane domain of CD28 and a signaling cytoplasmic domain such as 4-1BB (CD137), OX40 (CD134), DAP10, ICOS and CD3zeta chain (CD3). The most advanced application is the use of CAR-T cells targeting CD19, a surface antigen on B cell malignancies, which has demonstrated antitumor efficacy in patients with B cell malignancies (P. J. Paszkiewicz et al., Targeted antibody-mediated depletion of murine CD19 CAR T cells permanently reverses B cell aplasia. J Clin Invest 126, 4262-4272 (2016).

Results

In the design and development of TF-targeting CAR, factor VII was used, the natural ligand for TF, instead of antibody or scFv against TF, as recognition domain for TF. First, the affinity of fVII for TF (E. Waxman et al., Tissue factor and its extracellular soluble domain: the relationship between intermolecular association with factor VIIa and enzymatic activity of the complex. Biochemistry 31, 3998-4003 (1992)) is about 100- to 1000-fold greater than anti-body for TF antigen (L. Presta et al., Generation of a humanized, high affinity anti-tissue factor antibody for use as a novel antithrombotic therapeutic. Thrombosis and hae-mostasis 85, 379-389 (2001)). Second, fVII can be synthe-sized by recombinant DNA technology without the need for humanization of monoclonal antibodies or screening scFv libraries. Furthermore, it has been shown that the light chain of fVII (the first 152 amino acid residues) could bind equally or stronger than full-length fVII to TF-expressing human and murine cancer cells (Z. Hu et al., Targeting Tissue Factor for Immunotherapy of Triple-Negative Breast Cancer Using a Second-Generation ICON. Cancer Immunol Res 6, 671-684 (2018)). Thus, the TF-targeting CAR consists of human factor VII light chain as TF-targeting domain, without or with a hinge region of human IgG1, attached to CD28 transmembrane and cytoplasmic domains and then followed by cytoplasmic domains of 4-1BB and CD3ζ (FIG. 1), named TF-targeting CAR1 monomer and dimer (GenBank accession #MF806378 and MF806379, respectively, SEQ ID NOS: 1 and 2).

To efficiently transduce CAR constructs into NK cells, the CAR1 dimer and monomer cDNAs were subcloned into the multicloning site (MCS) of pCDH lentivector as it has successfully infected human NK line NK92 (Z. Hu, J. Cheng, J. Xu, W. Ruf, C. J. Lockwood, Tissue factor is an angiogenic-specific receptor for factor VII-targeted immu-notherapy and photodynamic therapy. Angiogenesis 20, 85-96 (2017)). The cDNA sequences of CAR1 monomer and dimer were confirmed by Sanger DNA sequencing and have been deposited at GenBank (accession #MF806378 and MF806379, SEQ ID NOS: 1 and 2).

To ensure that the pCDH plasmid and lentivirus (in supernatant and in PEG-it purified vector) can lead to CAR1 expression, pCDH plasmid encoding CAR1 (with GFP and Puro) was transfected into CHO-K1 and 293AD cells. CHO-K1 cells have been successfully transfected with pcDNA3.1(+) plasmid vectors for producing TF-targeting immunoconjugates fVII-IgG1Fc (called ICON) (Z. Hu et al., Targeting tissue factor as a novel therapeutic oncotarget for eradication of cancer stem cells isolated from tumor cell lines, tumor xenografts and patients of breast, lung and ovarian cancer. Oncotarget 8, 1481-1494 (2017); Z. Hu, A. Garen, Targeting tissue factor on tumor vascular endothelial cells and tumor cells for immunotherapy in mouse models of prostatic cancer. Proceedings of the National Academy of Sciences of the United States of America 98, 12180-12185 (2001); Z. Hu, J. Li, Natural killer cells are crucial for the efficacy of Icon (factor VII/human IgG1 Fc) immunotherapy in human tongue cancer. BMC immunology 11, 49 (2010) and fVIIL-IgG1Fc (called L-ICON1, for light chain ICON, as a second generation ICON) (Z. Hu et al., Targeting Tissue Factor for Immunotherapy of Triple-Negative Breast Cancer Using a Second-Generation ICON. Cancer Immunol Res 6, 671-684 (2018)Z. Hu, J. Cheng, J. Xu, W. Ruf, C. J. Lockwood, Tissue factor is an angiogenic-specific receptor for factor VII-targeted immunotherapy and photodynamic therapy. Angiogenesis 20, 85-96 (2017)). FIG. 3 shows that both CHO-K1 cells and 293AD cells expressed GFP after transfection with pCDH or lentivirus either in SNT or purified vector, indicating mammalian cells (hamster and human origins) can be transfected and infected by lentivirus. To generate CAR1-NK cells with the ability to mediate antibody-dependent cellular toxicity (ADCC), NK92MI (ATCC CRL-2408), a human NK cell line that was derived from parental line NK92 was transfected by stable transfec-tion with human IL-2 cDNA and is IL-2 independent. (K. Tam et al., Characterization of genetically altered, inter-leukin 2-independent natural killer cell lines suitable for adoptive cellular immunotherapy. Hum Gene Ther 10, 1359-1373 (1999)) Prior to lentivirus infection, NK92MI was also transfected with plasmid pcDNA3.1(+) encoding full length human CD16 (fCD16), a Fc receptor for IgG1Fc, in order to generate a CD16+NK cell line as effector cells to mediate antibody (such as ICON and L-ICON1)-dependent cellular cytotoxicity (ADCC). The resulting cells, designated as NK92MI/fCD16, were then infected by Lenti-CAR1 dimer and monomer vectors, which also encode GFP. FIG. 2 showed that after puromycin selection, stable NK92MI/fCD16 cells expressed GFP after infection with lentivirus vectors encoding CAR1 dimer and monomer (FIG. 2A) (abbreviated thereafter as CAR1 dimer and monomer, respectively), whereas uninfected NK92MI or NK92MI/fCD16 cells did not express GFP (as control cells), indicating that lentivirus has successfully infected the NK cell line NK92MI and its derivative NK92MI/fCD16.

Figure 4C:
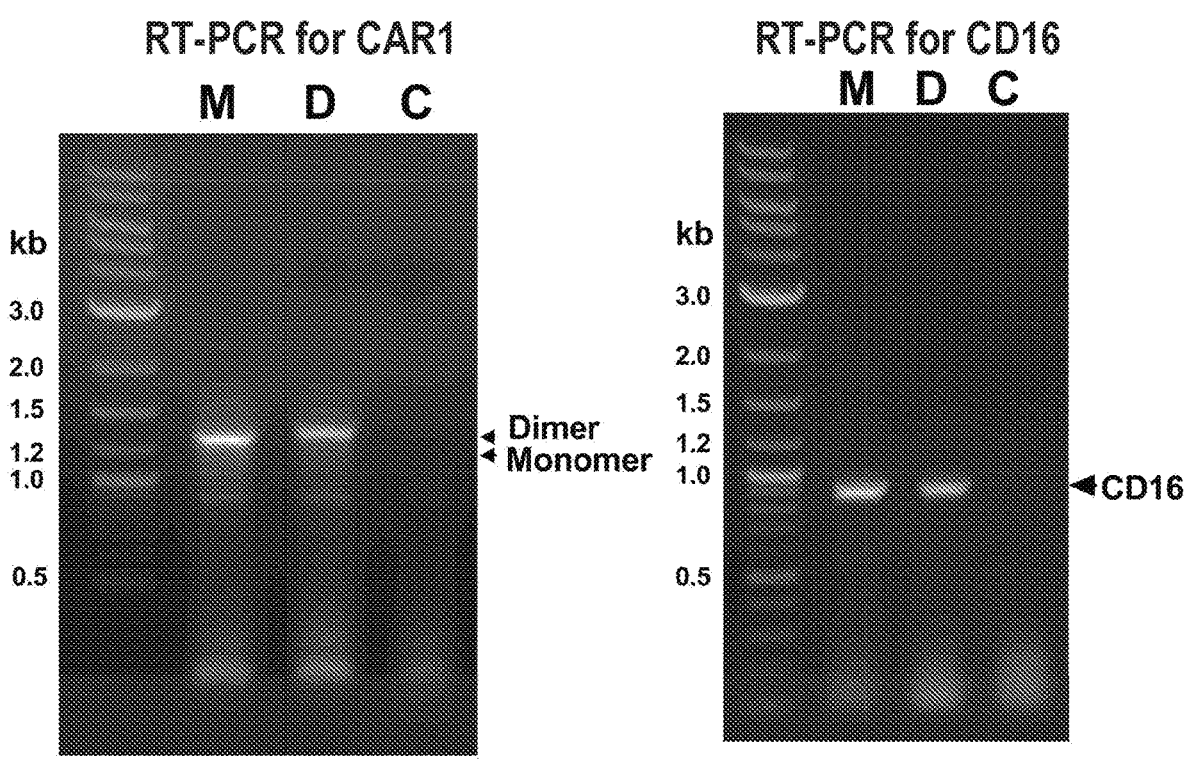
Figure 4C:
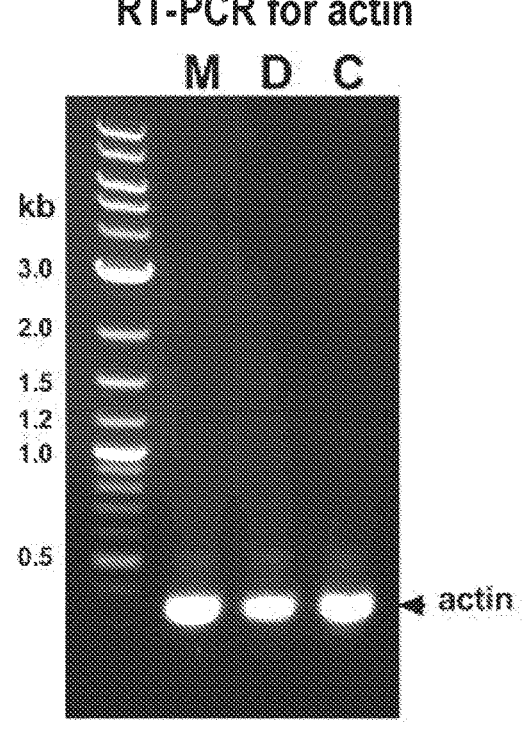
Figure 4D:
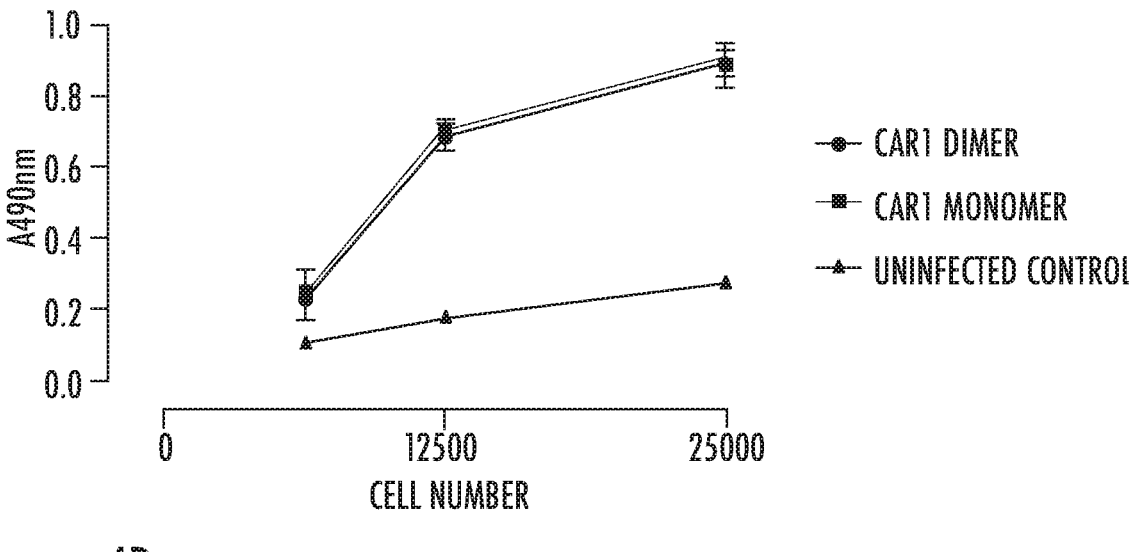

After establishing these stable CAR1-NK cell lines, the expression of CAR1 and CD16 cDNAs were verified in these cells by RT-PCR using specific primers (for example, fVIIL and CD3zeta for CAR1) and by ELISA using anti-human factor VII antibodies that we showed could recognize fVII light chain. FIG. 4a showed that cDNAs of CAR1 monomer and dimer were detected in NK92MI/fCD16/CAR1 monomer and dimer cells, respectively, and their molecular masses are consistent with their sequences, as shown in FIG. 1, whereas control NK92MI cells were negative for CAR1. FIG. 4b showed that CD16 cDNA was present in both NK92MI/fCD16/CAR1 monomer and dimer, but was absent in NK92MI control cells. Beta actin was used as a housekeeping gene control for equal amounts in RT-PCR assay (FIG. 4c).

Figure 5A:
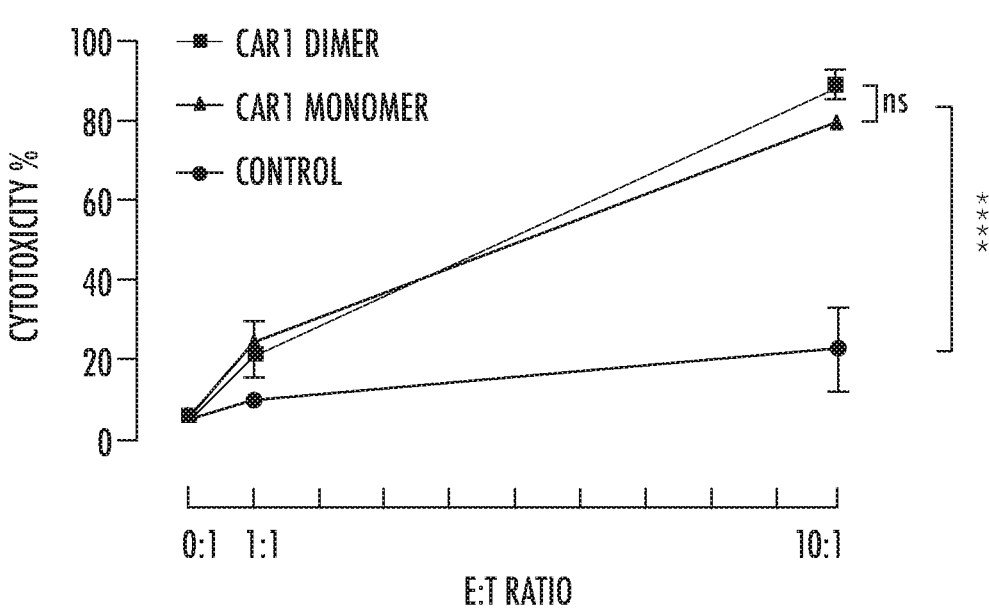
FIGS. 5A-D show cytotoxicity, efficacy and safety of TF-CAR-NK cells to TNBC cells in vitro and for the treatment of TNBC CDX in vivo in an orthotopic NSG mouse model. A. Cyotoxicity of NK-CAR1 dimer and monomer and NK control (Effector cells) to TNBC line (Target cells, MDA-MB-231) was assayed using CytoTox Homogenous Assay (Promega). CAR1 dimer and monomer: NK92MI cells expressing CD16 and TF-targeted CAR1 dimer or monomer. Control cells: Uninfected NK92MI (ATCC) as a NK control (negative in GFP, CD16 and CAR1). Note: Effector cells (E) were incubated directly with target cells (T) for assaying direct killing of TF-CAR-NK to TNBC. B-D: Tumor volume (B), tumor weight (C) and mouse body weight (D) of female NSG mice that were treated with one i.v. injection of $2 \times 10^6$ CAR1-NK cells or control NK cells on day 0. Data were analyzed by t test or ANOVA (Prism software) and were presented as mean+/−SEM.
Figure 5B:
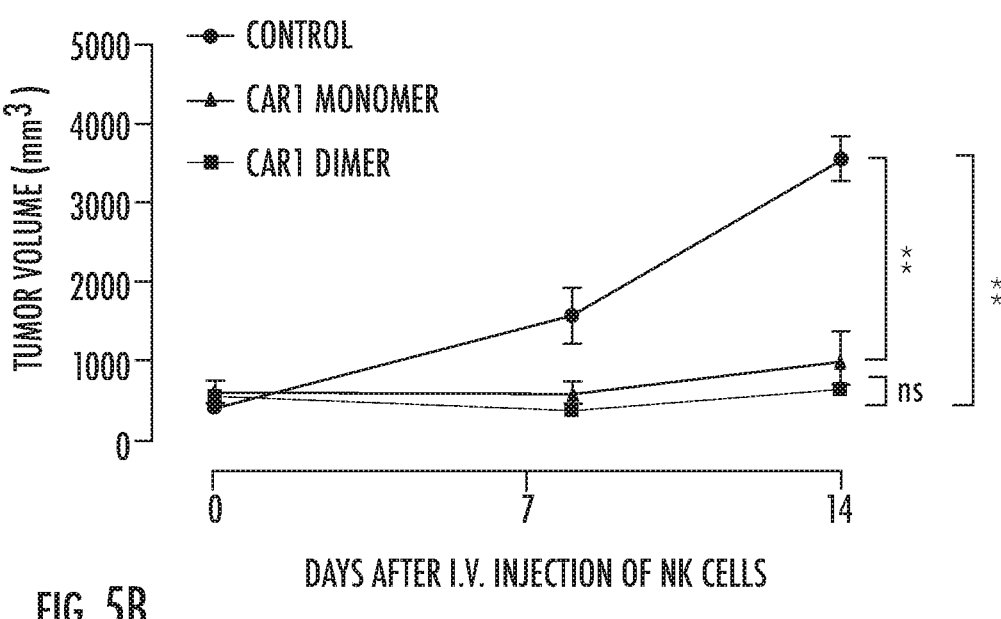
Figure 5C:
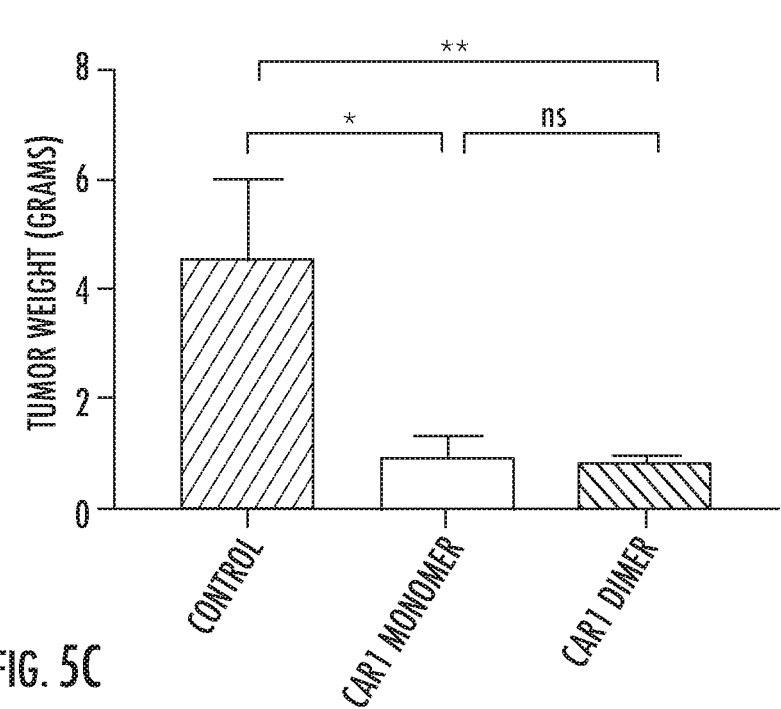
Figure 5D:
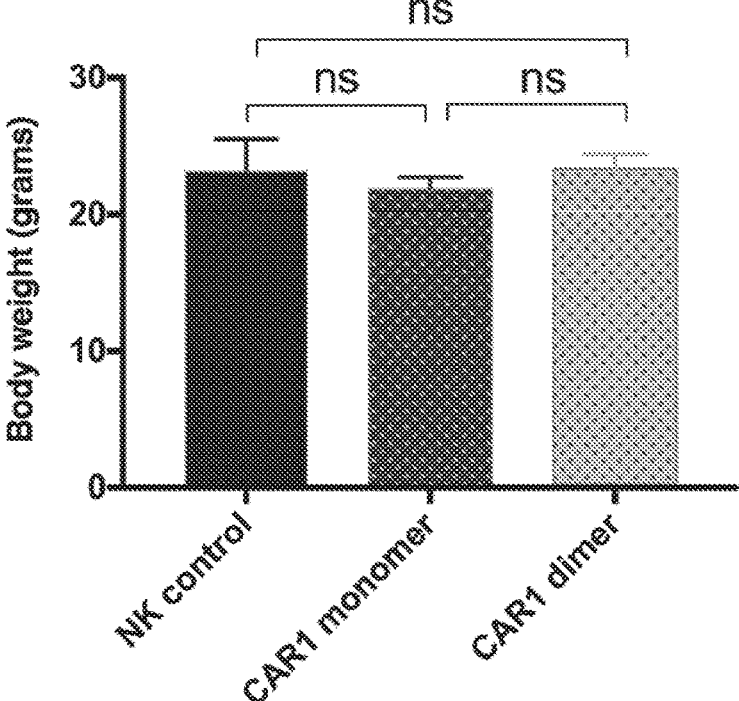

Having verified the expression of CAR1 and CD16 in NK-CAR1 monomer and dimer cells, their ability (cytotoxicity) to kill TNBC cells in vitro and the therapeutic efficacy and safety in vivo in an orthotopic TNBC CDX NSG mouse model was tested. FIG. 5A showed that both NK-CAR1 monomer and dimer cells exhibited significant direct cytotoxicity to human TNBC line MDA-MB-231 cells as compared to the control NK cells (p<0.0001, CAR1 monomer or dimer vs. control). Possibly due to avidity, CAR1 dimer showed slightly higher cytotoxicity (85%) to TNBC cells than that (77%) of CAR1 monomer at an E:T ratio of 10:1. However, the difference was not statistically significant (FIG. 5A). FIG. 5B-5D demonstrated that CAR1-NK monomer and dimer cells were effective and safe for the treatment of TNBC in an orthotopic CDX NSG mouse model. After a single i.v. injection of $2 \times 10^6$ NK-CAR1 monomer or dimer cells, TNBC CDX growth was significantly arrested as compared to those in control mice that were injected with non-lenti-CAR1-infected NK92MI/fCD16 control cells. Similar to our in vitro data, NK-CAR1 dimer cells were more effective for treating TNBC CDX than NK-CAR1 monomer, as evidenced by measuring tumor volume (FIG. 5B) and tumor weights (FIG. 5C), but the difference was not statistically significant. There was no difference in whole mouse body weights between control and NK-CAR1 treated groups (FIG. 5D), suggesting TF-targeted CAR1-NK therapy was safe. Since TF-CAR1 dimer cells had stronger effects than TF-CAR1 monomer cells for the treatment of TNBC in vitro and in vivo, NK-CAR1 dimer, but not monomer, cells were used in the subsequent studies.

Figure 6A:
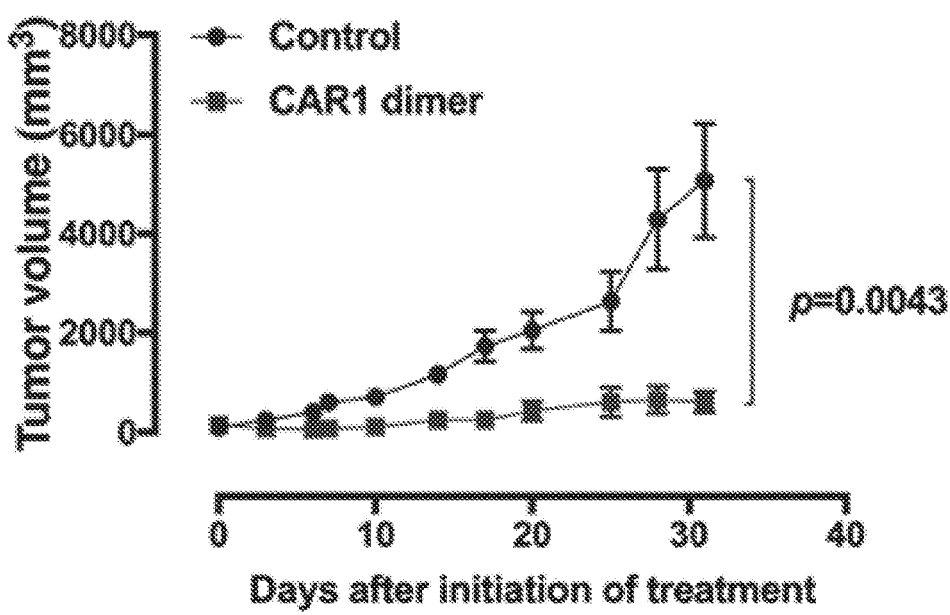
FIGS. 6A-C show TF-CAR-NK cell therapy was effective and safe in a pilot study for the treatment of human TNBC PDX in an orthotopic NSG mouse model. TNBC PDX (JAX) was generated in four-week-old female NSG mice. When the PDX tumors reached ~100 mm³, NK92MI expressing CAR1 dimer and CD16 (CAR1 dimer) were injected intravenously (i.v.) via tail veins ($3 \times 10^6$ cells per mouse, arrows) (three mice per group). Control mice were i.v. injected with NK92MI cells without CAR1.
Figure 6B:
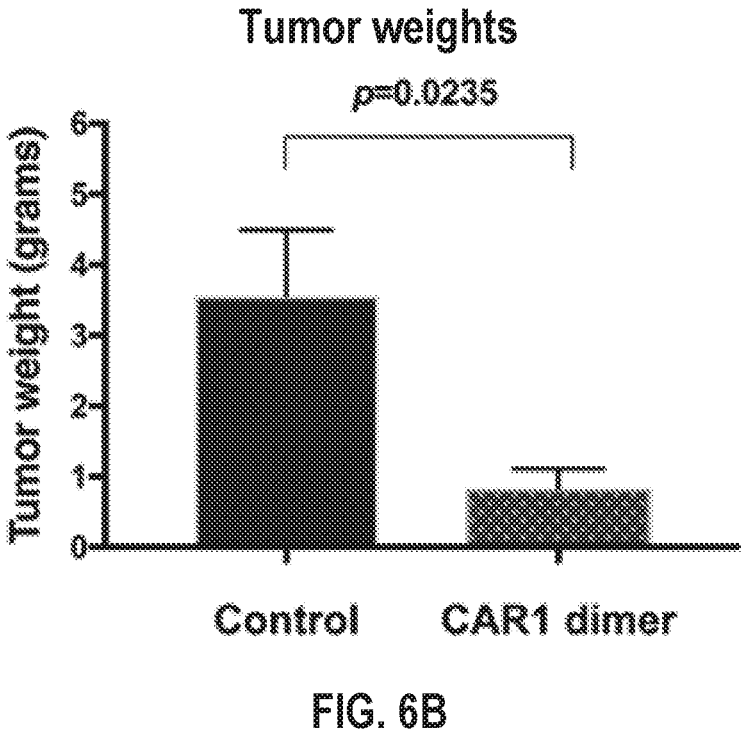
Figure 6C:
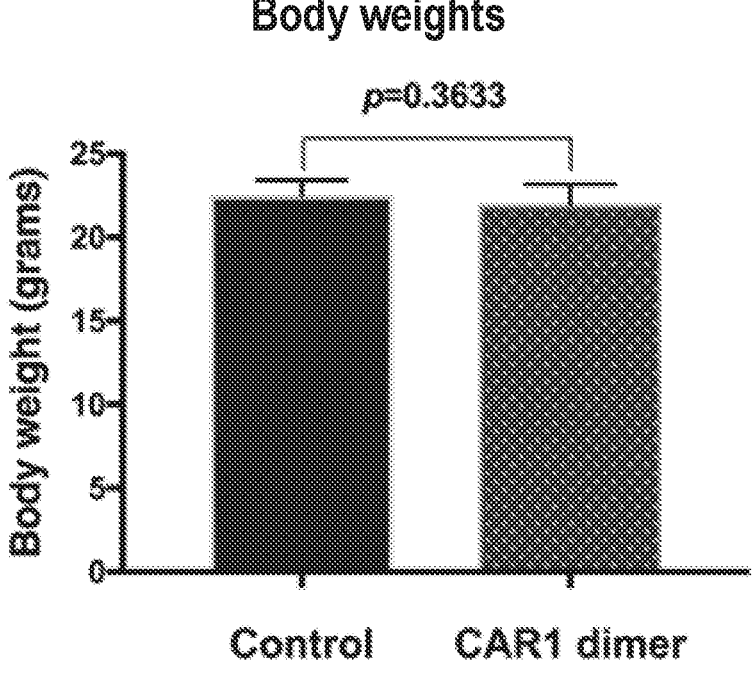

To better translate TF-CAR-NK therapy into the clinic, the efficacy and safety of NK-CAR1 cells were studied (3 mice per group) in an orthotpic TNBC PDX NSG mouse model. FIG. 6 demonstrated that TF-CAR1 dimer cell immunotherapy was effective and safe for the treatment of TNBC PDX in the orthotopic PDX NSG mouse model, as determined by measuring tumor volume (FIG. 6a), tumor weight (FIG. 6b) and mouse body weight (FIG. 6c).

Figure 7A:
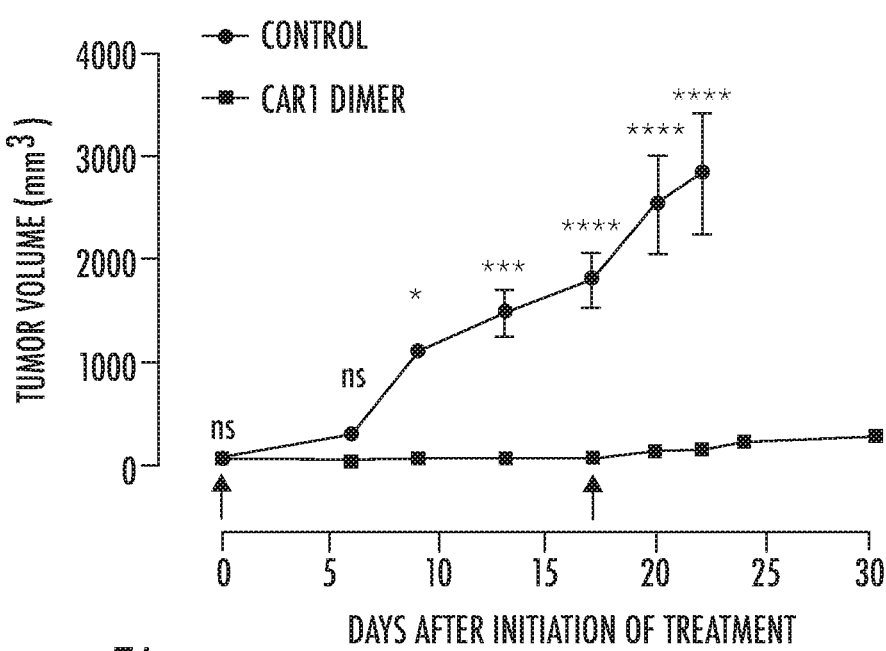
FIGS. 7A-D show TF-CAR-NK cell therapy was effective and safe for the treatment of human TNBC PDX in an orthotopic NSG mouse model. TNBC PDX (JAX) was generated in four-week old female NSG mice. When the PDX tumors reached ~100 mm³, NK92MI expressing CAR1 dimer and CD16 (CAR1 dimer) were injected i.v. via tail veins ($3 \times 10^6$ cells per mouse, arrows) (five mice per group). Parental NK92MI without CAR were used as control. a. Tumor volumes. b-c. Tumor weights and mouse body weights were measured at the time of sacrifice of animals. ns: no significance; *, *, **: $p < 0.05, 0.001$ and $0.0001$.
Figure 7B:
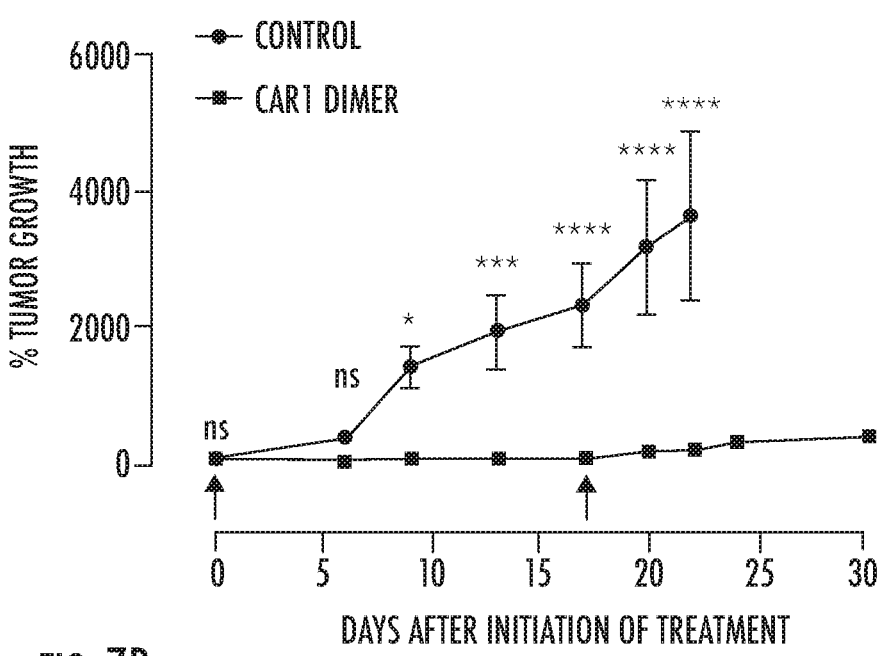
Figure 7C:
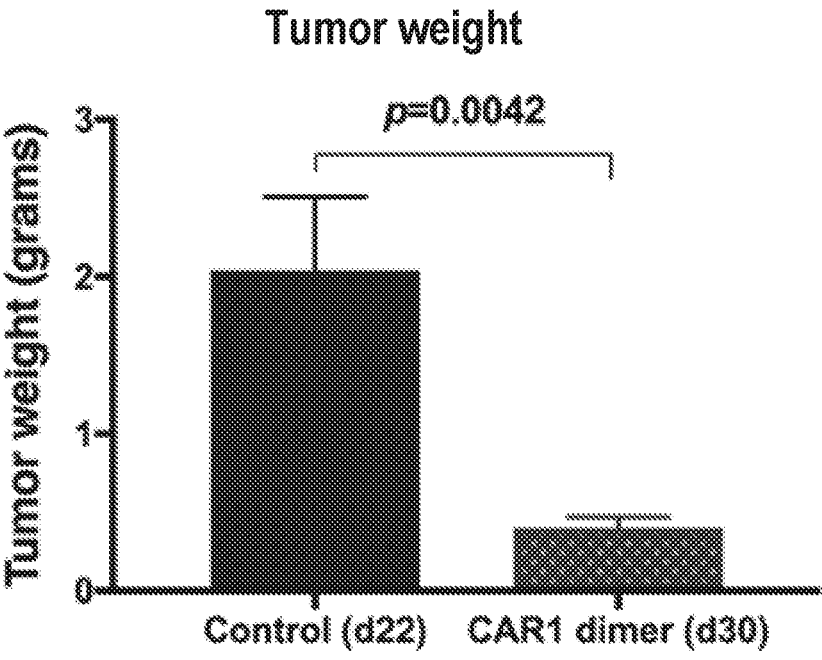
Figure 7D:
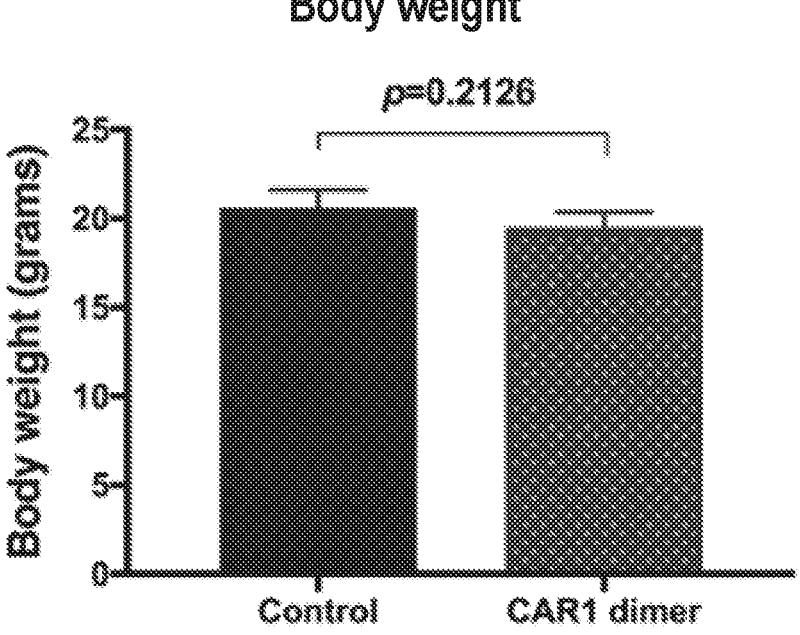

To verify the findings observed in the pilot study, the efficacy and safety study of TF-CAR1 dimer therapy in the orthotopic PDX NSG mice (5 mice per group) was repeated. FIG. 7 demonstrated that TF-targeting CAR1-NK cell immunotherapy was effective and safe for the treatment of TNBC PDX in preclinical mouse models, as determined by measuring tumor volume (FIG. 7A), tumor growth percentage (FIG. 7B), tumor weight (FIG. 7C) and mouse body weight (FIG. 7D).

DISCUSSION

To target TF for cellular immunotherapy, TF-targeting CAR-based lentivirus vectors were developed, and TF-CAR-NK cells generated by infecting a human NK line (NK92MI) with TF-CAR1 lentivirus vectors. It was shown that CAR1-NK cells, either with two or one TF-targeting domain(s) on each CAR construct, were effective and safe for the treatment of TNBC in vitro and in vivo in orthotopic CDX and PDX mouse models. Since these TF-CAR1 NK cells also express CD16, they can potentially mediate L-ICON1-ADCC in combination therapy with L-ICON1 and other therapeutic antibodies for the treatment of TNBC. Thus, this study established the proof of concept of targeting TF for CAR-NK cell immunotherapy of TNBC. TF is selectively expressed not only in cancer, but in pathological angiogenesis-dependent as well as macrophage-associated human diseases (Z. W. Hu, Therapeutic Antibody-Like Immunoconjugates against Tissue Factor with the Potential to Treat Angiogenesis-Dependent as Well as Macrophage-Associated Human Diseases. Antibodies 7, (2018)). Pathological angiogenesis, the formation of neovasculature, is involved in many clinically significant human diseases, notably cancer, age-related macular degeneration (AMD), endometriosis and rheumatoid arthritis (RA). Macrophages participate in the progression of a variety of human diseases, such as atherosclerosis and viral infections (human immunodeficiency virus, HIV and Ebola). It is well documented that TF is selectively expressed on angiogenic VECs in these pathological angiogenesis-dependent human diseases and on disease-associated macrophages. CAR-NK and -T therapies provide novel therapeutic approaches with the ability to treat these angiogenesis-dependent as well as macrophage-associated human diseases and, thus, can broadly impact the treatment regimen for these clinically significant human diseases.

Supporting Material and Methods for Example 2

Cell Lines

Chinese hamster ovary cells (CHO-K1) and NK92MI were purchased from American Type Culture Collection (ATCC, Manassas, VA) in 2004 and in 2007, respectively. CHO-K1 were grown in F12K complete growth medium (ATCC) supplemented with 10% heat-inactivated fetal bovine serum (HI-FBS) (Sigma) and 1× penicillin and streptomycin (Invitrogen). 293TN (SBI), 293FT (Invitrogen) and 293AD (Cell Biolabs) were purchased from commercial vendors and were grown in DMEM complete growth medium for production of lentivirus vectors. Human TNBC cell line MDA-MB-231 (BRCA1-wt, BRCA2-mutant) were purchased from ATCC in 2009 and were grown in L-15 complete growth medium supplemented with 10% HI-FBS and 1× penicillin and streptomycin (Invitrogen). Cultures were tested annually for mycoplasma contamination. The latest date they were tested by using Mycoalert Mycoplasma Detection Kit (Lonza, Cat. No. LT07-118) was Jun. 26, 2017. Authenticity of cancer cell lines was determined by validating TF expression by flow cytometry, Western blots and/or cell ELISA.

Construction of CAR Plasmid DNAs and Lentiviral Vectors

The TF-targeting CAR1 dimer and monomer constructs were designed to encode human factor VII light chain (as TF recognition domain) with human IgG1 hinge region (to form a homodimer of CAR1) or without the hinge region (as monomer CAR1) followed by CD28 transmembrane and cytoplasmic domain, 4-1BB and CD3 zeta. The cDNA constructs were custom synthesized into lentiviral shuttle vector pCDH (SBI Cat. No. CD713B) by System Biosciences (SBI). The cDNA sequences for TF-targeting CAR1 monomer and dimer were verified by Sanger DNA sequencing and were deposited at GenBank with accession numbers MF806378 and MF806379, respectively. The lentivirus encoding CAR1 dimer and monomer were produced by co-transfecting 293TN (System Biosciences) with pCDH-CAR1 and pPACKH1 (SBI) using PurFection transfection reagent (SBI) following the manufacturer's instructions. The lentivirus in cell culture supernatant was collected on 48 and 72 hours and used as unconcentrated viral particles in supernatant (SNT) or concentrated using PEG-it reagent (SBI).

Stable Expression of CAR1 Dimer, Monomer or Control GFP on Adherent (CHO-K1, 293AD) and Suspension Cells (NK92MI/fCD 16 and NK) by Lentivirus Infection and by Transfection with Expression Plasmid DNA The cells were infected with lentivirus in the presence of TransDUX and MAX Enhancer (SBI) following the manufacturer's instructions. Briefly, 50,000 cells per well of either adherent or suspension cells are seeded in a 24 well plate in cell culture medium. Next day, replace the cell culture medium with 500 µl infection medium, containing 2.5 µl of TransDux (SBI), 100 µl of MAX Enhancer and 400 µl culture medium then add 150 µl of 293TN lentivirus-containing supernatant (SNT) to each well and swirl to mix. 72 hours post-transduction, the viral genome will be integrated into the host cell genome and the cells are transferred and grown in complete growth medium supplemented with 5 µg/ml puromycin and 100 ng/ml hygromycin to establish stable cell lines or to use in the following experiments.

CD713B (SBI)-derived Plasmid DNA vectors expression CAR1 monomer, dimer or control were transfected by xTremeGene HP transfection reagent (Roche) into NK92 and NK92MI cells following the manufacturer's instructions. Briefly, 100,000 NK92 and NK92MI cells were seeded in 2 ml growth medium. On the same day, plasmid DNA (2 µg) was added to 200 µl Opti-Medium (serum free) followed by adding 6 µl X-tremeGENE HP transfection reagent and was incubated at room temperature for 15 min. The DNA transfection mix was added to each well in a drop-wise manner. 72 hours post transfection, puromycin was added to a final concentration of 5 µg/ml for selection of stably transfected cells.

Expression of CAR1 and CD16 on CAR1 NK Cells by RT-PCR and Western Blot

RT-PCR and Western blot were carried out to verify expression of CAR1 and CD16 on lentivirus-infected or plasmid transfected cells. Total RNAs were extracted from NK92MI/fCD16 control, CAR1 dimer and monomer cells using TriZol Reagent (Invitrogen). RT-PCR for CAR1, CD16 and beta actin was performed using One-Step RT-PCR kit (New England Biolabs, Cat. No. E5315) and corresponding primers and was analyzed by agarose gel electrophoresis.

Cytotoxicity of CAR1 NK Cells to Human TNBC Cells

Cytotoxicity assay was tested using CytoTox homogenous assay kits (Promega). Human TNBC MDA-MB-231 cells (target cells) were seeded 10,000 cells per well in 100 µl MEM alpha growth medium supplemented with 10% heat-inactivated FBS in 96-well U-bottom Tissue Culture-treated microplates overnight. Next morning, 50 µl medium was removed from each well. NK92MI/fCD16 expressing CAR1-dimer, -monomer or uninfected control (as effector cells) were resuspended in ADCC effector assay medium (DMEM with 0.5% super low IgG HI-FBS) and added to the wells at E:T ratio of 10:1 and 5:1. After 4 hours incubation at 5% $CO_2$ and 37° C., the microplate was centrifuged at 300×g for 5 min and 50 ul of supernatant was transferred to a new 96-well flat-bottom microplate. Cytoxtoxicity assay solution was added (50 ul per well) and incubated at 37C for 30 min before stop solution was added following the manufacturer's instruction. Absorbance at 490 nm was read on a microplate reader (Molecular Devices, i3).

Generation of orthotopic mouse models of TNBC cell-derived xenografts (CDX) and patient-derived xenografts (PDX). Briefly, to generate orthotopic mouse models of tumor line-derived xenografts, $5 \times 10^5$ human TNBC MDA-MB-231/Luc+GFP cells in 50 µl of PBS were injected into the fourth left mammary gland fat pad in 4-6 weeks-old, female NSG (Taconic Farms). To generate an orthotopic TNBC PDX model, a TNBC PDX donor NSG mouse (NOD SCID gamma, no mature B, T, NK cells and no complement) with BRCA1 mutation was purchased from Jackson Laboratory (JAX TM00089, breast tumor markers: TNBC ER–/PR–/HER2–, BRCA1 V757fs). Surgeries were performed in accordance with the OSU IACUC Rodent Surgery Policy. Mice were anesthetized with isoflurane. For the donor NSG mouse (JAX, TM00089), an incision was made over the flank of tumor to extract the tumor tissue, which was washed once in RPMI medium supplemented with 1× penicillin and streptomycin and was cut in sterile PBS into ~3 millimeters (mm) pieces in diameter for implantation into the recipient mice. CB-17 SCID mice (Taconic Farms) were used as recipient mice. For recipient mice, an incision was made over the fourth right mammary gland, for direct implantation of one piece of –3 mm PDX tumor tissues from the donor tumor tissue into it. One drop of tissue adhesive (Vetbond) and/or 1 wound clip (Sigma) was used to close the incision site in routine fashion. Animals were monitored for recovery from anesthesia before returning to routine husbandry. Animals were checked daily until wounds were healed, and analgesics (buprenorphine, s.c. 0.1 mg/kg in 100 µl sterile PBS) were administered to provide pain relief for up to 72 hours after surgery.

In vivo studies of TF-CAR-NK cell therapy. TNBC CDX and PDX (JAX) were generated in four-week-old female NSG mice. When the CDX or PDX tumors reached ~100-300 mm³, NK92MI expressing CD16 and CAR1 dimer or monomer (CAR1 dimer and monomer) were injected intravenously (i.v.) every two weeks via tail veins ($2$-$3 \times 10^6$ cells per mouse). Control mice were i.v. injected with NK92MI cells without CD16 nor CAR1. Therapeutic efficacy was determined by measuring tumor width (W) and length (L) with calipers in millimeters (mm) and calculating tumor volume (mm³) using the formula $(W)^2 \times L/2$ (mm³).

Statistical analysis. The data in vitro and in vivo are presented as mean+/–SEM and analyzed by ANOVA and t-test for statistical significance using Prism software (GraphPad). For analyses of statistical significance, duplicate or triplicate wells in each group were used for in vitro assays in tissue culture plates and 3 or 5 mice per group were used in vivo in animal studies. Statistical significance is presented as *: P<0.05; : P<0.01; *: P<0.001; ****: P<0.0001 and "ns" stands for no (statistical) significance.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Tables

TABLE 1

| Tissue factor expression in solid cancers, leukemia, sarcoma, lymphoma and myeloma | | | | |
|---|---|---|---|---|
| Type of tumor | Case number | % on TC | % on TVEC | References |
| Breast cancer | 115 | 81% | ND | (1) |
| | 7 | 100% | 100% | (2) |
| | 213 | 91% | 98.6% (stromal cells) | (3) |
| | Human chemoresistant breast tumor xenograft from mice * | + | + | (4) |
| Triple-negative breast cancer | 161 (14 whole tumor tissues and 147 tissue microarray tissues, TMA) | 85.7% of 14 whole tumor tissues 48.3% of 147 TMA Negative in matched normal breast tissues | 64.3% of 14 whole tumor tissues Negative on normal blood vessels in adjacent normal breast tissues | (5) |
| Melanoma | 41 primary 42 metastatic | 95% 100% | ND | (6) |
| | Human melanoma xenograft from mice * | + | + | (7) |
| Lung cancer | 25 | 28% | 78% (stromal macrophages, VECs) | (8) |
| | 191 (NSCLC) | 43% | ND | (9) |
| | 55 | 80% | ND | (10) |
| | 50 | 88% | ND | (11) |
| | 12 (snap-frozen adenocarcinoma NSCLC tissues) | 66.7% (8/12) moderately positive for flTF and 91.7% (11/12) for asTF** vs. the overall negative control healthy tissue | ND | (12) |
| Hepatocellular carcinoma (HCC) | 58 | 100% | ND | (13) |
| | 62 | 63% | ND | (14) |
| Pancreatic cancer | 55 | 53% | TF negative in normal pancreas | (15) |
| | 113 | 88.4% | ND | (16) |
| | 240 (10 normal pancreas 70 intraductal papillary mucinous neoplasms 40 pancreatic intraepithelial neoplasia, 130 resected or metastatic pancreatic adenocarcinomas) | 87.9% overall (77% pancreatic intraepithelial neoplasias 91% intraductal papillary mucinous neoplasms 89% pancreatic cancers) | ND (TF negative in normal pancreas) | (17) |
| Colorectal cancer | 67 primary, of which 18 with liver metastasis | 46% of primary, 88.9% of liver metastasis | ND | (18) |
| | 100 | 57.0% | ND | (19) |
| | 50 | 100% | ND | (20) |
| Prostate cancer | 67 | 73% | ND | (21) |
| | 73 | 75.3% | ND | (22) |
| | 32 early stage 22 advanced stage | 78% early-stage 60% advanced stage | ND (TF negative in benign prostate gland) | (23) |

TABLE 1-continued

| Tissue factor expression in solid cancers, leukemia, sarcoma, lymphoma and myeloma | | | | |
|---|---|---|---|---|
| Type of tumor | Case number | % on TC | % on TVEC | References |
| | Human prostate tumor in mice *** | + | + | (24) |
| Ovarian cancer | 32 | 84% | ND | (25) |
| Brain tumor | 44 (10 benign gliomas14 anaplastic astrocytomas 20 glioblastomas) | 75% overall (10% in Grade I-II, 86% in grade III 95% in grade IV) | ND | (26) |
| | 68 (23 glioblastomas 13 anaplastic astrocytomas 32 low-grade astrocytomas) | 47% overall (91.3% glioblastomas, 46.2% anaplastic astrocytomas, and 15.6% low-grade astrocytomas) | 44% overall (73.9% glioblastomas, 53.8% anaplastic astrocytomas, 0% low grade astrocytomas) | (27) |
| | 34 gliomas 5 normal brain tissues | 58.8% overall (20% of grade I 43% of grade II, 58% of grade III 90% of grade IV) | ND (TF negative in normal brain tissues) | (28) |
| | 90 gliomas (8 Low-grade astrocytoma 15 Anaplastic Astrocytoma 56 Glioblastoma 7 Anaplastic Oligoastrocytoma 4 Anaplastic Oligodendroglioma) 6 Embryonal tumors (1 Medulloblastoma 5 Primitive Neuroectodermal Tumor) | 82.1% overall (75% Low-grade astrocytoma 60% Anaplastic Astrocytoma 96.5% Glioblastoma 28.6% Analastic Oligoastrocytoma 75% Anaplastic Oligodendroglioma) 50% Overall (1/1 Medulloblastoma 2/5 Primitive Neuroectodermal Tumor) | | (29) |
| Leukemia | Human AML lines and leukemic cells from patients with AML | + | TF negative on the normal peripheral mononuclear cells unless stimulated by endotoxin or other cytokines (30) | (31-36) |
| | Human ALL lines and leukemic cells from patients with ALL | + | TF negative on myeloid precursor cells (32) | (37, 38) |
| Sarcoma | Mouse Meth-A sarcoma cells | + | | (39) |
| | Rat osteosarcoma cells | + | | (40) |
| | Kaposi's sarcoma**** | + | | (41) |
| Lymphoma | Hodgkin's lymphoma | + | | (42) |
| Myeloma | 18 Multiple myeloma (MM) patients and 3 MM lines | 56% (10/18) of MM patients + MM lines | | (43) |

1. U. Sturm et al., Immunohistological detection of tissue factor in normal and abnormal human mammary glands using monoclonal antibodies. *Virchows Archiv* 421, 79-86 (1992).

2. J. Contrino, G. Hair, D. L. Kreutzer, F. R. Rickles, In situ detection of tissue factor in vascular endothelial cells: correlation with the malignant phenotype of human breast disease. *Nat Med* 2, 209-215 (1996).

3. T. Ueno, M. Toi, M. Koike, S. Nakamura, T. Tominaga, Tissue factor expression in breast cancer tissues: its correlation with prognosis and plasma concentration. *British journal of cancer* 83, 164-170 (2000).

4. J. Duanmu, J. Cheng, J. Xu, C. J. Booth, Z. Hu, Effective treatment of chemoresistant breast cancer in vitro and in vivo by a factor VII-targeted photodynamic therapy. *British journal of cancer* 104, 1401-1409 (2011).

5. Z. Hu et al., Targeting Tissue Factor for Immunotherapy of Triple-Negative Breast Cancer Using a Second-Generation ICON. *Cancer Immunol Res*, (2018).

6. T. Kageshita et al., Tissue factor expression and serum level in patients with melanoma does not correlate with disease progression. *Pigment Cell Res* 14, 195-200 (2001).

7. Z. Hu, Y. Sun, A. Garen, Targeting tumor vasculature endothelial cells and tumor cells for immunotherapy of human melanoma in a mouse xenograft model. *Proceedings of the National Academy of Sciences of the United States of America* 96, 8161-8166 (1999).

8. M. Shoji et al., Activation of coagulation and angiogenesis in cancer: immunohistochemical localization in situ of clotting proteins and vascular endothelial growth factor in human cancer. *The American journal of pathology* 152, 399-411 (1998).

9. R. Koomagi, M. Volm, Tissue-factor expression in human non-small-cell lung carcinoma measured by immunohistochemistry: correlation between tissue factor and angiogenesis. *International journal of cancer* 79, 19-22 (1998).

10. M. Sawada et al., Expression of tissue factor in non-small-cell lung cancers and its relationship to metastasis. *British journal of cancer* 79, 472-477 (1999).

11. B. Wang et al., Radiotherapy of human xenograft NSCLC tumors in nude mice with a 90Y-labeled anti-tissue factor antibody. *Cancer biotherapy & radiopharmaceuticals* 20, 300-309 (2005).

12. P. Goldin-Lang et al., Tissue factor expression pattern in human non-small cell lung cancer tissues indicate increased blood thrombogenicity and tumor metastasis. *Oncol Rep* 20, 123-128 (2008).

13. R. T. Poon et al., Tissue factor expression correlates with tumor angiogenesis and invasiveness in human hepatocellular carcinoma. *Clin Cancer Res* 9, 5339-5345 (2003).

14. T. Kaido et al., Tissue factor is a useful prognostic factor of recurrence in hepatocellular carcinoma in 5-year survivors. *Hepato-gastroenterology* 52, 1383-1387 (2005).

15. A. K. Kakkar, N. R. Lemoine, M. F. Scully, S. Tebbutt, R. C. Williamson, Tissue factor expression correlates with histological grade in human pancreatic cancer. *The British journal of surgery* 82, 1101-1104 (1995).

16. N. Nitori et al., Prognostic significance of tissue factor in pancreatic ductal adenocarcinoma. *Clin Cancer Res* 11, 2531-2539 (2005).

17. A. A. Khorana et al., Tissue factor expression, angiogenesis, and thrombosis in pancreatic cancer. *Clin Cancer Res* 13, 2870-2875 (2007).

18. C. Shigemori et al., Tissue factor expression and metastatic potential of colorectal cancer. *Thromb Haemost* 80, 894-898 (1998).

19. T. Nakasaki et al., Expression of tissue factor and vascular endothelial growth factor is associated with angiogenesis in colorectal cancer. *Am J Hematol* 69, 247-254 (2002).

20. D. F. Altomare et al., Tissue factor and vascular endothelial growth factor expression in colorectal cancer: relation with cancer recurrence. *Colorectal Dis* 9, 133-138 (2007).

21. S. A. Abdulkadir et al., Tissue factor expression and angiogenesis in human prostate carcinoma. *Hum Pathol* 31, 443-447 (2000).

22. T. Akashi, Y. Furuya, S. Ohta, H. Fuse, Tissue factor expression and prognosis in patients with metastatic prostate cancer. *Urology* 62, 1078-1082 (2003).

23. V. Kaushal et al., Expression of tissue factor in prostate cancer correlates with malignant phenotype. *Appl Immunohistochem Mot Morphol* 16, 1-6 (2008).

24. Z. Hu, A. Garen, Targeting tissue factor on tumor vascular endothelial cells and tumor cells for immunotherapy in mouse models of prostatic cancer. *Proceedings* of the National Academy of Sciences of the United States of America 98, 12180-12185 (2001).

25. K. Uno et al., Tissue factor expression as a possible determinant of thromboembolism in ovarian cancer. *British journal of cancer* 96, 290-295 (2007).

26. K. Hamada et al., Expression of tissue factor correlates with grade of malignancy in human glioma. *Cancer* 77, 1877-1883 (1996).

27. S. Takano, K. Tsuboi, Y. Tomono, Y. Mitsui, T. Nose, Tissue factor, osteopontin, alphavbeta3 integrin expression in microvasculature of gliomas associated with vascular endothelial growth factor expression. *British journal of cancer* 82, 1967-1973 (2000).

28. M. Guan, J. Jin, B. Su, W. W. Liu, Y. Lu, Tissue factor expression and angiogenesis in human glioma. *Clin Biochem* 35, 321-325 (2002).

29. J. Thaler et al., Intratumoral tissue factor expression and risk of venous thromboembolism in brain tumor patients. *Thromb Res* 131, 162-165 (2013).

30. F. R. Rickles, G. A. Hair, R. A. Zeff, E. Lee, R. D. Bona, Tissue factor expression in human leukocytes and tumor cells. *Thromb Haemost* 74, 391-395 (1995).

31. K. Andoh et al., Tissue factor activity in leukemia cells. Special reference to disseminated intravascular coagulation. *Cancer* 59, 748-754 (1987).

32. K. A. Bauer et al., Tissue factor gene expression in acute myeloblastic leukemia. *Thromb Res* 56, 425-430 (1989).

33. H. Tanaka et al., Studies on leukemic cell tissue factor. *Thromb Res* 53, 535-549 (1989).

34. M. Tanaka, T. Kishi, Induction of tissue factor by interleukin-2 in acute myelogenous leukemia (AML) cells. *Growth Factors* 4, 1-8 (1990).

35. M. Tanaka, H. Yamanishi, The expression of tissue factor antigen and activity on the surface of leukemic cells. *Leuk Res* 17, 103-111 (1993).

36. T. Nakasaki et al., Elevated tissue factor levels in leukemic cell homogenate. *Clin Appl Thromb Hemost* 6, 14-17 (2000).

37. T. Kubota, K. Andoh, H. Sadakata, H. Tanaka, N. Kobayashi, Tissue factor released from leukemic cells. *Thromb Haemost* 65, 59-63 (1991).

38. T. Nakasaki et al., Decreased tissue factor and tissue-plasminogen activator antigen in relapsed acute promyelocytic leukemia. *Am J Hematol* 64, 145-150 (2000).

39. Y. Zhang et al., Intravenous somatic gene transfer with antisense tissue factor restores blood flow by reducing tumor necrosis factor-induced tissue factor expression and fibrin deposition in mouse meth-A sarcoma. *J Clin Invest* 97, 2213-2224 (1996).

40. J. G. Bledsoe, S. M. Slack, Tissue factor expression by rat osteosarcoma cells adherent to tissue culture polystyrene and selected orthopedic biomaterials. *J Biomater Sci Polym Ed* 9, 1305-1312 (1998).

41. Y. M. Zhang et al., Vascular origin of Kaposi's sarcoma. Expression of leukocyte adhesion molecule-1, thrombomodulin, and tissue factor. *The American journal of pathology* 144, 51-59 (1994).

42. G. Cesarman-Maus, E. Braggio, C. Lome-Maldonado, A. L. Morales-Leyte, R. Fonseca, Absence of tissue factor is characteristic of lymphoid malignancies of both T- and B-cell origin. *Thromb Res* 133, 606-609 (2014).

43. Gupta et al. Tissue Factor Is Frequently Expressed in Multiple Myeloma Cells. *Blood* 2009 114:2132; Abstract 2132

SEQUENCES
SEQUENCE ID NO 1: TF-targeting CAR1 monomer
GCTAGCGCCACCATGGTCTCCCAGGCCCTCAGGCTCCTCTGCCTTCTGCT

TGGGCTTCAGGGCTGCCTGGCTGCAGTCTTCGTAACCCAGGAGGAAGCCC

ACGGCGTCCTGCACCGGCGCCGGCGCGCCAACGCGTTCCTGGAGGAGCTG

CGGCCGGGCTCCCTGGAGAGGGAGTGCAAGGAGGAGCAGTGCTCCTTCGA

GGAGGCCCGGGAGATCTTCAAGGACGCGGAGAGGACGAAGCTGTTCTGGA

TTTCTTACAGTGATGGTGACCAGTGTGCCTCAAGTCCATGCCAGAATGGG

GGCTCCTGCAAGGACCAGCTCCAGTCCTATATCTGCTTCTGCCTCCCTGC

CTTCGAGGGCCGGAACTGTGAGACGCACAAGGATGACCAGCTGATCTGTG

TGAACGAGAACGGCGGCTGTGAGCAGTACTGCAGTGACCACACGGGCACC

AAGCGCTCCTGTCGGTGCCACGAGGGGTACTCTCTGCTGGCAGACGGGGT

GTCCTGCACACCCACAGTTGAATATCCATGTGGAAAAATACCTATTCTAG

AAAAAAGAAATGCCAGCAAGCCCCAAGGGCGAGGATCCTTTTGGGTGCTG

GTGGTGGTTGGTGGAGTCCTGGCTTGCTATAGCTTGCTAGTAACAGTGGC

CTTTATTATTTTCTGGGTGAGGAGTAAGAGGAGCAGGCTCCTGCACAGTG

ACTACATGAACATGACTCCCCGCCGCCCCGGGCCCACCCGCAAGCATTAC

CAGCCCTATGCCCCACCACGCGACTTCGCAGCCTATCGCTCCTTCGAACG

TTTCTCTGTTGTTAAACGGGGCAGAAAGAAACTCCTGTATATATTCAAAC

AACCATTTATGAGACCAGTACAAACTACTCAAGAGGAAGATGGCTGTAGC

TGCCGATTTCCAGAAGAAGAAGAAGGAGGATGTGAACTGGAATTCAGAGT

GAAGTTCAGCAGGAGCGCAGACGCCCCCGCGTACCAGCAGGGCCAGAACC

AGCTCTATAACGAGCTCAATCTAGGACGAAGAGAGGAGTACGATGTTTTG

GACAAGAGACGTGGCCGGGACCCTGAGATGGGGGGAAAGCCGAGAAGGAA

GAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGG

CACGATGGCCTTTACCAGGGTCTCAGTACAGCCACCAAGGACACCTACGA

CGCCCTTCACATGCAGGCCCTGCCCCCTCGCTGAGTTTAAACGCGGCCGC
Diagram of CAR1 monomer (hfVIIL-CD28-4-1BB-
CD3zeta)
<u>NheI</u>-Kozak-fVII light chain (Start codon +
signal + mature fVII light chain)-<u>BamHI</u>-CD28
(TM + CD)-<u>BstBI</u>-4-1BB-<u>EcoRI</u>-CD3zeta CD-Stop
codon-<u>PmeI</u>-<u>NotI</u>

Sequence ID NO: 2: TF-targeting CAR1 Dimer
GCTAGCGCCACCATGGTCTCCCAGGCCCTCAGGCTCCTCTGCCTTCTGCT

TGGGCTTCAGGGCTGCCTGGCTGCAGTCTTCGTAACCCAGGAGGAAGCCC

ACGGCGTCCTGCACCGGCGCCGGCGCGCCAACGCGTTCCTGGAGGAGCTG

CGGCCGGGCTCCCTGGAGAGGGAGTGCAAGGAGGAGCAGTGCTCCTTCGA

GGAGGCCCGGGAGATCTTCAAGGACGCGGAGAGGACGAAGCTGTTCTGGA

TTTCTTACAGTGATGGTGACCAGTGTGCCTCAAGTCCATGCCAGAATGGG

GGCTCCTGCAAGGACCAGCTCCAGTCCTATATCTGCTTCTGCCTCCCTGC

CTTCGAGGGCCGGAACTGTGAGACGCACAAGGATGACCAGCTGATCTGTG

TGAACGAGAACGGCGGCTGTGAGCAGTACTGCAGTGACCACACGGGCACC

AAGCGCTCCTGTCGGTGCCACGAGGGGTACTCTCTGCTGGCAGACGGGGT

GTCCTGCACACCCACAGTTGAATATCCATGTGGAAAAATACCTATTCTAG

AAAAAAGAAATGCCAGCAAGCCCCAAGGGCGAGGATCCGCAGAGCCCAAA

TCTTGTGACAAAACTCACACATGCCCACCGTGCCCAGGATCCTTTTGGGT

GCTGGTGGTGGTTGGTGGAGTCCTGGCTTGCTATAGCTTGCTAGTAACAG

TGGCCTTTATTATTTTCTGGGTGAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGCTCCTTCG

AACGTTTCTCTGTTGTTAAACGGGGCAGAAAGAAACTCCTGTATATATTC

AAACAACCATTTATGAGACCAGTACAAACTACTCAAGAGGAAGATGGCTG

TAGCTGCCGATTTCCAGAAGAAGAAGAAGGAGGATGTGAACTGGAATTCA

GAGTGAAGTTCAGCAGGAGCGCAGACGCCCCCGCGTACCAGCAGGGCCAG

AACCAGCTCTATAACGAGCTCAATCTAGGACGAAGAGAGGAGTACGATGT

TTTGGACAAGAGACGTGGCCGGGACCCTGAGATGGGGGGAAAGCCGAGAA

GGAAGAACCCTCAGGAAGGCCTGTACAATGAACTGCAGAAAGATAAGATG

GCGGAGGCCTACAGTGAGATTGGGATGAAAGGCGAGCGCCGGAGGGGCAA

GGGGCACGATGGCCTTTACCAGGGTCTCAGTACAGCCACCAAGGACACCT

ACGACGCCCTTCACATGCAGGCCCTGCCCCCTCGCTGAGTTTAAACGCGG

CCGC
Diagram of hfVIIL-hinge-CD28-4-1BB-CD3zeta
<u>NheI</u>-Kozak-fVII light chain (Start codon +
signal + mature fVII light chain)-<u>BamHI*</u>-hIgG1
hinge-<u>BamHI*</u>-CD28 (TM + CD)-<u>BstBI</u>-4-1BB-<u>EcoRI</u>-
CD3zeta CD-Stop codon-<u>PmeI</u>-<u>NotI</u>
TM: Transmembrane domain. CD: Cytoplasmic
domain. NheI, BamHI, BstBI, EcoRI, PmeI and
NotI: Restriction enzymes are used for mole-
cular subcloning of individual recognition and
signaling fragments into plasmid constructs and
allows for modification of CAR signaling frag-
ments, for example, replacing 4-1BB with OX40
(TF-targeting CAR2) or adding OX40 to CAR1 as a
fourth generation CAR (TF-targeting CAR3).

SEQ ID NO: 3: cDNA sequence of human coagulation
factor VII light chain
ATGGTCTCCCAGGCCCTCAGGCTCCTCTGCCTTCTGCTTGGGCTTCAGGG

CTGCCTGGCTGCAGTCTTCGTAACCCAGGAGGAAGCCCACGGCGTCCTGC

ACCGGCGCCGGCGCGCCAACGCGTTCCTGGAGGAGCTGCGGCCGGGCTCC

CTGGAGAGGGAGTGCAAGGAGGAGCAGTGCTCCTTCGAGGAGGCCCGGGA

GATCTTCAAGGACGCGGAGAGGACGAAGCTGTTCTGGATTTCTTACAGTG

ATGGTGACCAGTGTGCCTCAAGTCCATGCCAGAATGGGGGCTCCTGCAAG

GACCAGCTCCAGTCCTATATCTGCTTCTGCCTCCCTGCCTTCGAGGGCCG

GAACTGTGAGACGCACAAGGATGACCAGCTGATCTGTGTGAACGAGAACG

GCGGCTGTGAGCAGTACTGCAGTGACCACACGGGCACCAAGCGCTCCTGT

CGGTGCCACGAGGGGTACTCTCTGCTGGCAGACGGGGTGTCCTGCACACC

CACAGTTGAATATCCATGTGGAAAAATACCTATTCTAGAAAAAAGAAATG

CCAGCAAGCCCCAAGGGCGA

-continued

```
SEQ ID NO: 4: a 38-amino acid signal peptide
(underlined) followed by 152-amino acid mature
fVII light chain peptide
MVSQALRLLC LLLGLQGCLA AVFVTQEEAH GVLHRRRRAN

AFLEELRPGS LERECKEEQC SFEEAREIFK DAERTKLFWI

SYSDGDQCAS SPCQNGGSCK DQLQSYICFC LPAFEGRNCE

THKDDQLICV NENGGCEQYC SDHTGTKRSC RCHEGYSLLA

DGVSCTPTVE YPCGKIPILE KRNASKPQGR //
```

REFERENCES

1. Hu, Y., Tian, Z. G., and Zhang, C. (2018). Chimeric antigen receptor (CAR)-transduced natural killer cells in tumor immunotherapy. Acta Pharmacol Sin 39, 167-176.
2. Liu, E., Tong, Y., Dotti, G., Shaim, H., Savoldo, B., Mukherjee, M., Orange, J., Wan, X., Lu, X., Reynolds, A., et al. (2018). Cord blood NK cells engineered to express IL-15 and a CD19-targeted CAR show long-term persistence and potent antitumor activity. Leukemia 32, 520-531.
3. Mehta, R. S., and Rezvani, K. (2018). Chimeric Antigen Receptor Expressing Natural Killer Cells for the Immunotherapy of Cancer. Front Immunol 9, 283.
4. Nowakowska, P., Romanski, A., Miller, N., Odendahl, M., Bonig, H., Zhang, C., Seifried, E., Wels, W. S., and Tonn, T. (2018). Clinical grade manufacturing of genetically modified, CAR-expressing NK-92 cells for the treatment of ErbB2-positive malignancies. Cancer Immunol Immunother 67, 25-38.
5. Adorno-Cruz et al., Cancer stem cells: targeting the roots of cancer, seeds of metastasis, and sources of therapy resistance. Cancer research 75, 924-929 (2015).
6. Afuwape, et al., The role of the angiogenic molecule VEGF in the pathogenesis of rheumatoid arthritis. Histology and histopathology, 17(3):961-972 (2002).
7. Anders, et al., Biology, metastatic patterns, and treatment of patients with triple-negative breast cancer. Clinical breast cancer 9 Suppl 2, S73-81 (2009).
8. Bayraktar, et al., Molecularly targeted therapies for metastatic triple-negative breast cancer. Breast cancer research and treatment 138, 21-35 (2013).
9. Berrada, et al., Treatment of triple-negative metastatic breast cancer: toward individualized targeted treatments or chemosensitization? Annals of oncology: official journal of the European Society for Medical Oncology/ESMO 21 Suppl 7, vii30-35 (2010).
10. Bora et al., Immunotherapy for choroidal neovascularization in a laser-induced mouse model simulating exudative (wet) macular degeneration. Proceedings of the National Academy of Sciences of the United States of America 100, 2679-2684 (2003).
11. Bromberg, et al., Tissue factor promotes melanoma metastasis by a pathway independent of blood coagulation. Proceedings of the National Academy of Sciences of the United States of America 92, 8205-8209 (1995).
12. Caine, et al., The hypercoagulable state of malignancy: pathogenesis and current debate. Neoplasia 4, 465-473 (2002).
13. Callander, et al., Immunohistochemical identification of tissue factor in solid tumors. Cancer 70, 1194-1201 (1992).

14. Chen et al., A combinational therapy of EGFR-CAR NK cells and oncolytic herpes simplex virus 1 for breast cancer brain metastases. Oncotarget 7, 27764-27777 (2016).
15. Cheng et al., Effective Treatment of Human Lung Cancer by Targeting Tissue Factor with a Factor VII-Targeted Photodynamic Therapy. Curr Cancer Drug Targets 11, 1069-1081 (2011).
16. Clarke et al., Cancer stem cells—perspectives on current status and future directions: AACR Workshop on cancer stem cells. Cancer research 66, 9339-9344 (2006).
17. Contrino, et al., In situ detection of tissue factor in vascular endothelial cells: correlation with the malignant phenotype of human breast disease. Nature medicine 2(2):209-215 (1996).
18. Contrino, et al., In situ characterization of antigenic and functional tissue factor expression in human tumors utilizing monoclonal antibodies and recombinant factor VIIa as probes. Am J Pathol 145, 1315-1322 (1994).
19. Duanmu, et al., Effective treatment of chemoresistant breast cancer in vitro and in vivo by a factor VII-targeted photodynamic therapy. British journal of cancer. 104(9): 1401-1409 (2011).
20. El Guerrab et al., Differential impact of EGFR-targeted therapies on hypoxia responses: implications for treatment sensitivity in triple-negative metastatic breast cancer. PloS one 6, e25080 (2011).
21. Ferrandina, et al., Targeting CD133 antigen in cancer. Expert Opin Ther Targets 13, 823-837 (2009).
22. Ferrara N. VEGF and the quest for tumour angiogenesis factors. Nature reviews Cancer. 2(10):795-803 (2002).
23. Folkman, Tumor angiogenesis and tissue factor. Nat Med 2, 167-168 (1996).
24. Fujimoto, et al., Angiogenesis in endometriosis and angiogenic factors. Gynecologic and obstetric investigation 48 Suppl 1:14-20 (1999).
25. Hu et al., Tissue factor is an angiogenic-specific receptor for factor VII-targeted immunotherapy and photodynamic therapy. Angiogenesis (2016).
26. Hu, et al., Factor VII-Targeted Photodynamic Therapy for Breast Cancer and Its Therapeutic Potential for Other Solid Cancers and Leukemia, Breast Cancer—Current and Alternative Therapeutic Modalities, Esra Gunduz and Mehmet Gunduz (Ed.), ISBN: 978-953-307-776-5, InTech, E. Gunduz, Gunduz, M., Ed., Breast Cancer—Current and Alternative Therapeutic Modalities (InTech, 2011), pp. 175-196.
27. Hu, et al., Intratumoral injection of adenoviral vectors encoding tumor-targeted immunoconjugates for cancer immunotherapy. Proceedings of the National Academy of Sciences of the United States of America 97, 9221-9225 (2000).
28. Hu, et al., Natural killer cells are crucial for the efficacy of Icon (factor VII/human IgG1 Fc) immunotherapy in human tongue cancer. BMC immunology 11, 49 (2010).
29. Hu, et al., Selective and effective killing of angiogenic vascular endothelial cells and cancer cells by targeting tissue factor using a factor VII-targeted photodynamic therapy for breast cancer. Breast cancer research and treatment 126(3):589-600 (2011).
30. Hu, et al., Targeting tissue factor as a novel therapeutic oncotarget for eradication of cancer stem cells isolated from tumor cell lines, tumor xenografts and patients of breast, lung and ovarian cancer. Oncotarget, (2016).
31. Hu, et al., Targeting Tissue Factor for Immunotherapy of Triple-Negative Breast Cancer Using a Second-Generation ICON. Cancer Immunol Res 6, 671-684 (2018).

32. Hu, et al., Targeting tissue factor on tumor vascular endothelial cells and tumor cells for immunotherapy in mouse models of prostatic cancer. Proc Natl Acad Sci USA 98, 12180-12185 (2001).

33. Hu, et al., Targeting tissue factor on tumour cells and angiogenic vascular endothelial cells by factor VII-targeted verteporfin photodynamic therapy for breast cancer in vitro and in vivo in mice. BMC cancer 10:235 (2010).

34. Hu, et al., Targeting tumor vasculature endothelial cells and tumor cells for immunotherapy of human melanoma in a mouse xenograft model. Proceedings of the National Academy of Sciences of the United States of America 96, 8161-8166 (1999).

35. Hu, et al., Therapeutic Antibody-Like Immunoconjugates against Tissue Factor with the Potential to Treat Angiogenesis-Dependent as Well as Macrophage-Associated Human Diseases. Antibodies 7, (2018).

36. Hu, et al., Tissue factor is an angiogenic-specific receptor for factor VII-targeted immunotherapy and photodynamic therapy. Angiogenesis 20, 85-96 (2017).

37. Hudis, et al., Triple-negative breast cancer: an unmet medical need. The oncologist 16 Suppl 1, 1-11 (2011).

38. Hufnagel et al., Icon immunoconjugate treatment results in regression of red lesions in a non-human primate (Papio anubis) model of endometriosis. Reprod Biol 18, 109-114 (2018).

39. Jemal et al., Global cancer statistics. CA: a cancer journal for clinicians 61, 69-90 (2011).

40. Kassam et al., Survival outcomes for patients with metastatic triple-negative breast cancer: implications for clinical practice and trial design. Clinical breast cancer 9, 29-33 (2009).

41. Kasthuri, M. B. Taubman, N. Mackman, Role of tissue factor in cancer. J Clin Oncol 27, 4834-4838 (2009).

42. Kim, et al. Mapping the site on human IgG for binding of the MHC class I-related receptor, FcRn. European journal of immunology 29, 2819-2825, doi:10.1002/(SICI)1521-4141(199909)29:09< 2819::AID-IMMU2819> 3.0.CO; 2-6 (1999).

43. Klagsbrun, et al., Purification of endothelial cell growth factors by heparin affinity chromatography. Methods in enzymology 147:95-105 (1987).

44. Koch, et al., Cancer stem cells at the crossroads of current cancer therapy failures—radiation oncology perspective. Seminars in cancer biology 20(2):116-124 (2010).

45. Konigsberg, et al., Molecular cloning of the cDNA for human tissue factor. Cell 52(5):639-640 (1988).

46. Krikun et al., The immunoconjugate "icon" targets aberrantly expressed endothelial tissue factor causing regression of endometriosis. Am J Pathol 176, 1050-1056 (2010).

47. Liedtke, et al., Current Issues of Targeted Therapy in Metastatic Triple-Negative Breast Cancer. Breast care 6, 234-239 (2011).

48. Lopez-Pedrera, et al., Tissue factor as an effector of angiogenesis and tumor progression in hematological malignancies. Leukemia 20, 1331-1340 (2006).

49. Lykke, e al., The role of tissue factor in colorectal cancer. Eur J Surg Oncol 29, 417-422 (2003).

50. Milsom et al., Tissue factor and cancer stem cells: is there a linkage? Arterioscler Thromb Vasc Biol 29, 2005-2014 (2009).

51. Moncharmont, et al., Targeting a cornerstone of radiation resistance: cancer stem cell. Cancer letters 322(2):139-147 (2012).

52. Montero, et al., Bevacizumab in the treatment of metastatic breast cancer: friend or foe? Current oncology reports 14, 1-11 (2012).

53. Morrissey, et al., Molecular cloning of the cDNA for tissue factor, the cellular receptor for the initiation of the coagulation protease cascade. Cell 50, 129-135 (1987).

54. Mousa, Role of current and emerging antithrombotics in thrombosis and cancer. Timely topics in medicine. Cardiovascular diseases 10, E19 (2006).

55. Nemerson, Tissue factor and the initiation of blood coagulation. Advances in experimental medicine and biology 214:83-94 (1987).

56. Nemerson, Tissue factor and hemostasis. Blood 71, 1-8 (1988).

57. Osterud, Tissue factor: a complex biological role. Thrombosis and haemostasis 78, 755-758 (1997).

58. Paszkiewicz, et al., Targeted antibody-mediated depletion of murine CD19 CAR T cells permanently reverses B cell aplasia. J Clin Invest 126, 4262-4272 (2016).

59. Peitzsch, A et al., Cancer stem cells: The root of tumor recurrence and metastases. Semin Cancer Biol 44, 10-24 (2017).

60. Penka, [Activation of blood coagulation in oncology patients]. Vnitrni lekarstvi 43, 337-339 (1997).

61. Phillips, et al., The response of CD24(-/low)/CD44+ breast cancer-initiating cells to radiation. Journal of the National Cancer Institute 98, 1777-1785 (2006).

62. Presta et al., Generation of a humanized, high affinity anti-tissue factor antibody for use as a novel antithrombotic therapeutic. Thrombosis and haemostasis 85, 379-389 (2001).

63. Rak, et al., Tissue factor in cancer and angiogenesis: the molecular link between genetic tumor progression, tumor neovascularization, and cancer coagulopathy. Seminars in thrombosis and hemostasis 32, 54-70 (2006).

64. Rakha, et al., Metastatic triple-negative breast cancer. Clinical oncology 23, 587-600 (2011).

65. Rao, et al., Tissue factor on cells. Blood Coagul Fibrinolysis 9 Suppl 1, S27-35 (1998).

66. Rickles, et al., The role of the hemostatic system in tumor growth, metastasis, and angiogenesis: tissue factor is a bifunctional molecule capable of inducing both fibrin deposition and angiogenesis in cancer. Int J Hematol 73, 145-150 (2001).

67. Ruf, et al., Tissue factor and cell signalling in cancer progression and thrombosis. J Thromb Haemost 9 Suppl 1, 306-315 (2011).

68. Semeraro, et al., Tissue factor in health and disease. Thrombosis and haemostasis 78, 759-764 (1997).

69. Sheridan et al., CD44+/CD24-breast cancer cells exhibit enhanced invasive properties: an early step necessary for metastasis. Breast Cancer Res 8, R59 (2006).

70. Spicer, et al., Isolation of cDNA clones coding for human tissue factor: primary structure of the protein and cDNA. Proceedings of the National Academy of Sciences of the United States of America 84(15) 5148-5152 (1987).

71. Stapleton, et al. Competition for FcRn-mediated transport gives rise to short half-life of human IgG3 and offers therapeutic potential. Nature communications 2, 599, doi:10.1038/ncomms1608 (2011).

72. Tam, et al., Characterization of genetically altered, interleukin 2-independent natural killer cell lines suitable for adoptive cellular immunotherapy. Hum Gene Ther 10, 1359-1373 (1999).

73. Tang, et al., Mapping of angiogenic markers for targeting of vectors to tumor vascular endothelial cells. Cancer Gene Ther 14, 346-353 (2007).

74. Tezel, et al., Targeting tissue factor for immunotherapy of choroidal neovascularization by intravitreal delivery of factor VII-Fc chimeric antibody. Ocul Immunol Inflamm 15, 3-10 (2007).

75. Versteeg, et al., Tissue factor and cancer metastasis: the role of intracellular and extracellular signaling pathways. Mol Med 10, 6-11 (2004).

76. Vidal, et al., Targeting cancer stem cells to suppress acquired chemotherapy resistance. Oncogene 33(36), 4451-4463 (2014).

77. Waxman, et al., Tissue factor and its extracellular soluble domain: the relationship between intermolecular association with factor VIIa and enzymatic activity of the complex. Biochemistry 31, 3998-4003 (1992).

78. Yoshida, How to eliminate MYCN-positive hepatic cancer stem cells to prevent the recurrence? Proceedings of the National Academy of Sciences of the United States of America 115, E6388-E6389 (2018).

What is claimed is:

1. A natural killer (NK) cell composition comprising a chimeric antigen receptor (CAR), wherein the CAR comprises a human factor VII (fVII) light chain peptide, and wherein the CAR is encoded by a nucleic acid comprising SEQ ID NO: 1 or SEQ ID NO: 2.

2. The NK cell composition of claim 1, wherein the human light chain fVII comprises amino acids 39 to 190 of SEQ ID NO: 4.

* * * * *